(12) United States Patent
Cully et al.

(10) Patent No.: US 8,231,650 B2
(45) Date of Patent: Jul. 31, 2012

(54) EMBOLIC FILTER FRAME HAVING LOOPED SUPPORT STRUT ELEMENTS

(75) Inventors: Edward H. Cully, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 1287 days.

(21) Appl. No.: 11/020,809

(22) Filed: Dec. 22, 2004

(65) Prior Publication Data

US 2005/0101989 A1    May 12, 2005

Related U.S. Application Data

(63) Continuation of application No. 10/273,859, filed on Oct. 17, 2002, now abandoned.

(51) Int. Cl.
*A61M 29/00* (2006.01)
(52) U.S. Cl. .................................. 606/200; 604/96.01
(58) Field of Classification Search .................. 606/159, 606/194, 198, 200; 604/22, 96, 96.01, 103.01
See application file for complete search history.

(56) References Cited

U.S. PATENT DOCUMENTS

| | | | |
|---|---|---|---|
| 4,374,026 A | 2/1983 | Greutert | |
| 4,425,908 A | 1/1984 | Simon | 128/1 R |
| 4,723,549 A | 2/1988 | Wholey et al. | 128/344 |
| 5,133,733 A | 7/1992 | Rasmussen et al. | 606/200 |
| 5,192,286 A * | 3/1993 | Phan et al. | 606/127 |
| 5,634,942 A | 6/1997 | Chevillon et al. | |
| 5,695,518 A | 12/1997 | Laerum | |
| 5,695,519 A | 12/1997 | Summers et al. | 606/200 |

(Continued)

FOREIGN PATENT DOCUMENTS

EP    0812155    12/2003

(Continued)

OTHER PUBLICATIONS

Gunther RW and Vorwerk D. Minibasket for Percutaneous Embolectomy and Filter Protection Against Distal Embolization: Technical Note. Cardiovasc Intervent Radiol 1991; 14:195-98.

(Continued)

*Primary Examiner* — Victor Nguyen
(74) *Attorney, Agent, or Firm* — Fish & Richardson P.C.

(57) ABSTRACT

An improved embolic filter frame having looped support struts. The frame configuration provides enhanced longitudinal compliance, improved sealing against a vessel wall, low profile delivery, and a short deployed length. The looped support struts have a high degree of "radial" stiffness with a low degree of "longitudinal" stiffness. In the deployed state, the frame exerts a relatively high stress onto a vessel wall to maintain an effective seal, yet remains compliant in the longitudinal direction. Minor displacements of the support wire or catheter are therefore not translated to the filter. The looped support struts elongate when tensioned and assume a compressed and essentially linear form. While constrained in this linear state by a delivery catheter, the support struts exert minimal stress onto the delivery system. The overall delivery profile and stiffness are therefore reduced. When the delivery catheter constraint is removed during deployment, the struts "snap open" and assume a looped configuration which exert a high degree of force onto the vessel wall, creating an enhanced filter to vessel wall seal. In addition, the looped struts and the central collar connecting the support struts to the support wire, are positioned essentially within the plane of the filter opening. The overall deployed length of the embolic filter is therefore reduced.

11 Claims, 16 Drawing Sheets

U.S. PATENT DOCUMENTS

| | | | |
|---|---|---|---|
| 5,709,704 A | 1/1998 | Nott et al. ............... 606/200 |
| 5,735,892 A | 4/1998 | Myers et al. ............. 606/198 |
| 5,769,816 A | 6/1998 | Barbut et al. ............... 604/96 |
| 5,814,064 A | 9/1998 | Daniel et al. ............. 606/200 |
| 5,827,324 A | 10/1998 | Cassell et al. |
| 5,853,420 A | 12/1998 | Chevillon et al. |
| 5,876,367 A | 3/1999 | Kaganov et al. |
| 5,893,869 A | 4/1999 | Barnhart et al. |
| 5,902,475 A | 5/1999 | Trozera et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,941,869 A | 8/1999 | Patterson et al. |
| 5,941,896 A | 8/1999 | Kerr |
| 5,980,552 A | 11/1999 | Pinchasik et al. |
| 5,980,555 A | 11/1999 | Barbut et al. ............. 606/200 |
| 5,989,281 A | 11/1999 | Barbut et al. ............. 606/200 |
| 6,001,118 A | 12/1999 | Daniel et al. |
| 6,027,520 A | 2/2000 | Tsugita et al. ............. 606/200 |
| 6,042,598 A * | 3/2000 | Tsugita et al. ............. 606/200 |
| 6,051,014 A | 4/2000 | Jang |
| 6,051,015 A | 4/2000 | Maahs |
| 6,053,932 A | 4/2000 | Daniel et al. |
| 6,058,914 A | 5/2000 | Suzuki |
| 6,059,814 A | 5/2000 | Ladd |
| 6,066,149 A | 5/2000 | Samson et al. |
| 6,068,645 A | 5/2000 | Tu |
| 6,074,357 A | 6/2000 | Kaganov et al. |
| 6,083,215 A | 7/2000 | Milavetz |
| 6,090,097 A | 7/2000 | Barbut et al. ............. 604/511 |
| 6,099,549 A | 8/2000 | Bosma et al. |
| 6,117,154 A | 9/2000 | Barbut et al. ............. 606/181 |
| 6,129,739 A | 10/2000 | Khosravi |
| 6,136,016 A | 10/2000 | Barbut et al. ............. 606/200 |
| 6,142,987 A | 11/2000 | Tsugita |
| 6,146,370 A | 11/2000 | Barbut |
| 6,152,946 A | 11/2000 | Broome et al. ............. 606/200 |
| 6,152,947 A | 11/2000 | Ambrisco et al. |
| 6,168,603 B1 | 1/2001 | Leslie et al. ............. 606/114 |
| 6,168,604 B1 | 1/2001 | Cano ..................... 606/114 |
| 6,168,622 B1 | 1/2001 | Mazzocchi |
| 6,171,327 B1 * | 1/2001 | Daniel et al. ............. 606/200 |
| 6,171,328 B1 | 1/2001 | Addis |
| 6,171,329 B1 | 1/2001 | Shaw et al. ............. 606/213 |
| 6,179,859 B1 | 1/2001 | Bates et al. ............. 606/200 |
| 6,187,025 B1 | 2/2001 | Machek |
| 6,224,612 B1 | 5/2001 | Bates et al. |
| 6,231,544 B1 | 5/2001 | Tsugita et al. ............. 604/104 |
| 6,231,589 B1 | 5/2001 | Wessman et al. |
| 6,235,045 B1 | 5/2001 | Barbut et al. ............. 606/200 |
| 6,277,139 B1 | 8/2001 | Levinson et al. ............. 606/200 |
| 6,327,772 B1 | 12/2001 | Zadno-Azizi et al. |
| 6,346,117 B1 | 2/2002 | Greenhalgh ............. 606/200 |
| 6,361,546 B1 | 3/2002 | Khosravi ............. 606/200 |
| 6,364,895 B1 | 4/2002 | Greenhalgh ............. 606/200 |
| 6,371,969 B1 | 4/2002 | Tsugita et al. ............. 606/200 |
| 6,371,970 B1 | 4/2002 | Khosravi et al. ............. 606/200 |
| 6,375,670 B1 | 4/2002 | Greenhalgh ............. 606/200 |
| 6,391,037 B1 | 5/2002 | Greenhalgh ............. 606/151 |
| 6,391,044 B1 * | 5/2002 | Yadav et al. ............. 606/200 |
| 6,432,122 B1 | 8/2002 | Gilson et al. ............. 606/200 |
| 6,485,501 B1 | 11/2002 | Green ............. 606/200 |
| 6,511,496 B1 | 1/2003 | Huter et al. ............. 606/200 |
| 6,511,497 B1 | 1/2003 | Braun et al. |
| 6,517,559 B1 | 2/2003 | O'Connell ............. 606/158 |
| 6,544,279 B1 * | 4/2003 | Hopkins et al. ............. 606/200 |
| 6,558,405 B1 | 5/2003 | McInnes |
| 6,575,996 B1 | 6/2003 | Denison et al. |
| 6,599,307 B1 | 7/2003 | Huter et al. ............. 606/200 |
| 6,610,077 B1 | 8/2003 | Hancock et al. |
| 6,730,117 B1 | 5/2004 | Tseng et al. |
| 6,939,361 B1 | 9/2005 | Kleshinski |
| 6,939,362 B2 | 9/2005 | Boyle et al. |
| 7,241,304 B2 * | 7/2007 | Boyle et al. ............. 606/200 |
| 7,306,618 B2 * | 12/2007 | Demond et al. ............. 606/200 |
| 7,338,510 B2 | 3/2008 | Boylan et al. |
| 2001/0044634 A1 | 11/2001 | Don Michael et al. |
| 2001/0044652 A1 | 11/2001 | Moore |
| 2002/0038767 A1 | 4/2002 | Trozera |
| 2002/0088531 A1 | 7/2002 | Cook et al. |
| 2003/0065354 A1 | 4/2003 | Boyle et al. |
| 2003/0065355 A1 | 4/2003 | Weber |
| 2003/0139764 A1 | 7/2003 | Levinson et al. ............. 606/200 |
| 2003/0144688 A1 | 7/2003 | Brady et al. ............. 606/200 |
| 2003/0187474 A1 | 10/2003 | Keegan et al. ............. 606/200 |

FOREIGN PATENT DOCUMENTS

| | | |
|---|---|---|
| EP | 1566148 | 8/2005 |
| GB | 2337002 | 11/1999 |
| WO | 9833443 | 8/1998 |
| WO | WO 98/33443 | 8/1998 |
| WO | 99/23976 | 5/1999 |
| WO | 99/44542 | 9/1999 |
| WO | 00/07521 | 2/2000 |
| WO | WO 00/16705 | 3/2000 |
| WO | WO 00/49970 | 8/2000 |
| WO | 00/67665 | 11/2000 |
| WO | 01/08595 | 2/2001 |
| WO | 01/19231 | 3/2001 |
| WO | 01/19260 | 3/2001 |
| WO | 01/45569 | 6/2001 |
| WO | 01/49215 | 7/2001 |
| WO | 03/011188 | 2/2003 |
| WO | 03/017823 | 3/2003 |
| WO | 03/035130 | 5/2003 |
| WO | 03/055412 | 7/2003 |
| WO | 03/063732 | 8/2003 |
| WO | 03/077799 | 9/2003 |

OTHER PUBLICATIONS

International Search Report and Written Opinion for PCT/US03/32962 (WO 04/034884).

Bamford J, et al. Incidence of Stroke in Oxfordshire: First Year's Experience of a Community Stroke Register. British Medical Journal 1983; 287:713-717.

Barnett et al. Beneficial Effect of Carotid Endarterectomy. NE Journal of Medicine 1991; 325(7):446-453.

Hankey GJ. Investigation and Imaging Strategies in Acute Stroke and Transient Ischaemic Attacks. Hospital Update 1992; 107-124.

Robins M, et al. The National Survey of Stroke: The National Institute of Neurological and Communicative Disorders and Stroke. Office of Biometry and Field Studies Report. Chapter 4. Incidence. Stroke 1981; Part II; 12 (2):I-45 to I-57.

Theron JG et al. Carotid Artery Stenosis: Treatment With Protected Balloon Angioplasty and Stent Placement. Radiology 1996; 201:627-636.

Theron J, et al. New Triple Coaxial Catheter System for Carotid Angioplasty with Cerebral Protection. Amer J of Neuroradiology 1990; 11:869-874.

Yadav JS, et al. Elective Stenting of the Extracranial Carotid Arteries. Circulation 1997; 95:376-381.

Executive Committee for the Asymptomatic Carotid Atherosclerosis Study. Endarterectomy for Asymptomatic Carotid Artery Stenosis. JAMA 1995; 273(18): 1421-1461.

European Search Report, EP09007542, Jul. 28, 2009, Munich, 4 pages.

* cited by examiner

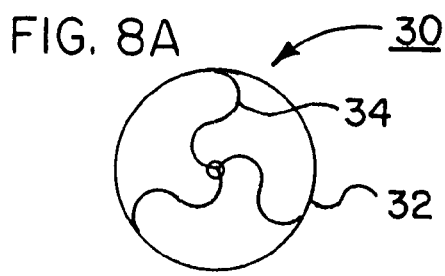
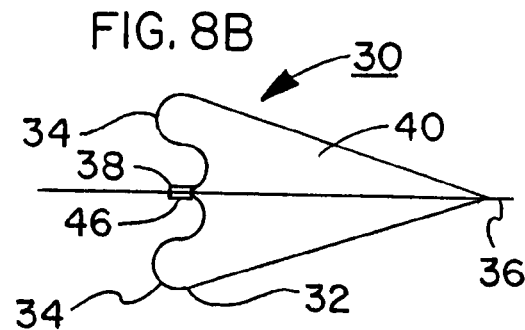
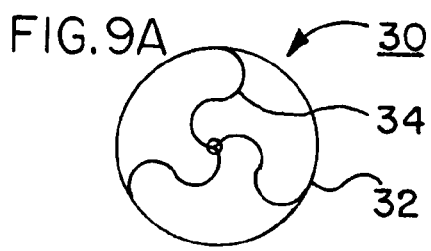
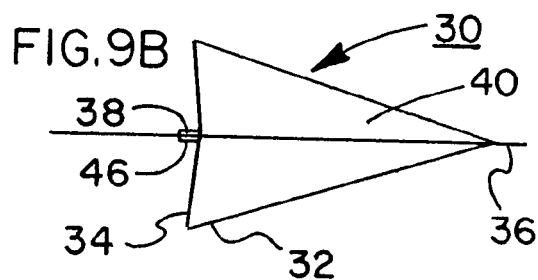
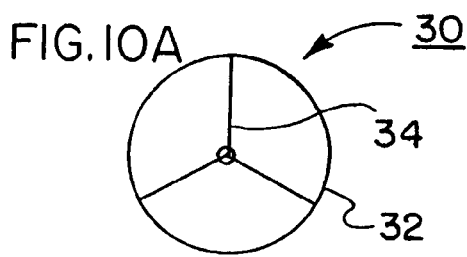
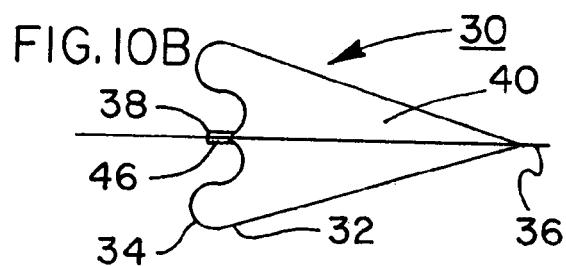
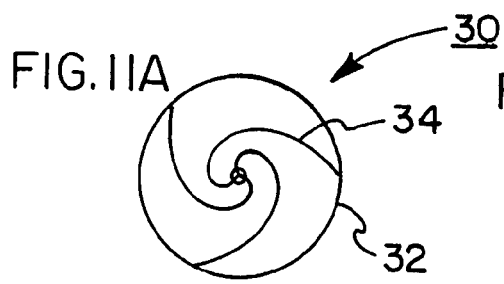
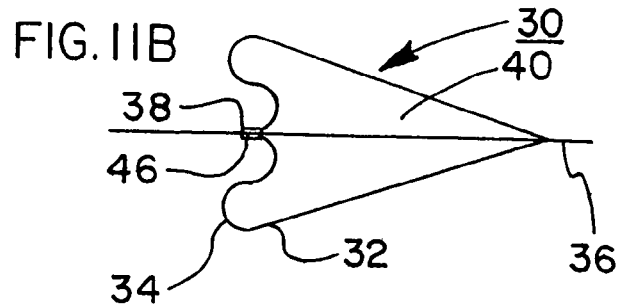

EMBOLIC FILTER FRAME HAVING LOOPED SUPPORT STRUT ELEMENTS

CROSS REFERENCE TO RELATED APPLICATIONS

This application is a continuation of U.S. patent application Ser. No. 10/273,859 filed Oct. 17, 2002, now abandoned.

FIELD OF THE INVENTION

The invention relates to embolic filter devices for placement in the vasculature and in particular, self-expanding frames used to support embolic filter elements.

BACKGROUND OF THE INVENTION

Embolic protection is a concept of growing clinical importance directed at reducing the risk of embolic complications associated with interventional (i.e., transcatheter) and surgical procedures. In therapeutic vascular procedures, liberation of embolic debris (e.g., thrombus, clot, atheromatous plaque, etc.) can obstruct perfusion of the downstream vasculature, resulting in cellular ischemia and/or death. The therapeutic vascular procedures most commonly associated with adverse embolic complications include: carotid angioplasty with or without adjunctive stent placement; and revascularization of degenerated saphenous vein grafts. Additionally, percutaneous transluminal coronary angioplasty (PTCA) with or without adjunctive stent placement, surgical coronary artery by-pass grafting, percutaneous renal artery revascularization, and endovascular aortic aneurysm repair have also been associated with complications attributable to atheromatous embolization. The use of embolic protection devices to capture and remove embolic debris, consequently, may improve patient outcomes by reducing the incidence of embolic complications.

Embolic protection devices typically act as an intervening barrier between the source of the clot or plaque and the downstream vasculature. Numerous devices and methods of embolic protection have been used adjunctively with percutaneous interventional procedures. These techniques, although varied, have a number of desirable features including: intraluminal delivery; flexibility; trackability; small delivery profile to allow crossing of stenotic lesions; dimensional compatibility with conventional interventional implements; ability to minimize flow perturbations; thromboresistance; conformability of the barrier to the entire luminal cross section (even if irregular); and a means of safely removing the embolic protection device and trapped particulates. There are two general strategies for achieving embolic protection: techniques that employ occlusion balloons; and techniques that employ an embolic filter. The use of embolic filters is a desirable means of achieving embolic protection because they allow continuous perfusion of the vasculature downstream to the device.

Occlusion balloon techniques have been taught by the prior art and involve devices in which blood flow to the vasculature distal to the lesion is blocked by the inflation of an occlusive balloon positioned downstream to the site of intervention. Following therapy, the intraluminal compartment between the lesion site and the occlusion balloon is aspirated to evacuate any thrombus or atheromatous debris that may have been liberated during the interventional procedure. The principle drawback of occlusion balloon techniques stems from the fact that during actuation, distal blood flow is completely inhibited, which can result in ischemic pain, distal stasis/thrombosis, and difficulties with fluoroscopic visualization due to contrast wash-out through the treated vascular segment.

A prior system described in U.S. Pat. No. 4,723,549 to Wholey, et al. combines a therapeutic catheter (e.g., angioplasty balloon) and integral distal embolic filter. By incorporating a porous filter or embolus barrier at the distal end of a catheter, such as an angioplasty balloon catheter, particulates dislodged during an interventional procedure can be trapped and removed by same therapeutic device responsible for the embolization. One known device includes a collapsible filter device positioned distal to a dilating balloon on the end of the balloon catheter. The filter comprises a plurality of resilient ribs secured to circumference of the catheter that extend axially toward the dilating balloon. Filter material is secured to and between the ribs. The filter deploys as a filter balloon is inflated to form a cup-shaped trap. The filter, however, does not necessarily seal around the interior vessel wall. Thus, particles can pass between the filter and the vessel wall. The device also lacks longitudinal compliance. Thus, inadvertent movement of the catheter results in longitudinal translation of the filter, which can cause damage to the vessel wall and liberate embolic debris.

Other prior systems combine a guide wire and an embolic filter. The embolic filters are incorporated directly into the distal end of a guide wire system for intravascular blood filtration. Given the current trends in both surgical and interventional practice, these devices are potentially the most versatile in their potential applications. These systems are typified by a filter frame that is attached to a guide wire that mechanically supports a porous filter element. The filter frame may include radially oriented struts, one or more circular hoops, or a pre-shaped basket configuration that deploys in the vessel. The filter element is typically comprised of a polymeric or metallic mesh net, which is attached to the filter frame and/or guide wire. In operation, blood flowing through the vessel is forced through the mesh filter element thereby capturing embolic material in the filter.

Early devices of this type are described in the art, for example in U.S. Pat. No. 5,695,519 to Summers, et al., and include a removable intravascular filter mounted on a hollow guide wire for entrapping and retaining emboli. The filter is deployable by manipulation of an actuating wire that extends from the filter into and through the hollow tube and out the proximal end. During positioning within a vessel, the filter material is not fully constrained so that, as the device is positioned through and past a clot, the filter material can potentially snag clot material creating freely floating emboli prior to deployment. The device also lacks longitudinal compliance.

Another example of a prior device, taught in U.S. Pat. No. 5,814,064 to Daniel, et al., uses an emboli capture device mounted on the distal end of a guide wire. The filter material is coupled to a distal portion of the guide wire and is expanded across the lumen of a vessel by a fluid activated expandable member in communication with a lumen running the length of the guide wire. During positioning, as the device is passed through and beyond the clot, filter material may interact with the clot to produce emboli. The device also lacks longitudinal compliance.

Another device, taught in U.S. Pat. No. 6,152,946 to Broome, et al., which is adapted for deployment in a body vessel for collecting floating debris and emboli in a filter, includes a collapsible proximally tapered frame to support the filter between a collapsed insertion profile and an expanded deployment profile. The tapered collapsible frame includes a mouth that is sized to extend to the walls of the body vessel in the expanded deployed profile and substantially longitudinal struts that attach and tether the filter frame to the support wire. This device also lacks substantial longitudinal compliance. This device has the additional drawback of having an extended length due to the longitudinally oriented strut configuration of the tapered frame. This extended length complicates the navigation and placement of the filter within tortuous anatomy.

A further example of an embolic filter system, found in PCT WO 98/33443, involves a filter material fixed to cables or spines of a central guide wire. A movable core or fibers inside the guide wire can be utilized to transition the cables or spines from approximately parallel to the guide wire to approximately perpendicular the guide wire. The filter, however, may not seal around the interior vessel wall. Thus, particles can pass between the filter and the entire vessel wall. This umbrella-type device is shallow when deployed so that, as it is being closed for removal, particles have the potential to escape.

In summary, disadvantages associated with predicate devices include lack of longitudinal compliance, extended deployed length of the frame and associated tethering elements, and inadequate apposition and sealing against a vessel wall. Without longitudinal compliance, inadvertent movement of the filter catheter or support wire can displace the deployed filter and damage a vessel wall and/or introgenic vascular trauma, or, in extreme cases, result in the liberation of embolic debris. An extended deployed length aggravates proper filter deployment adjacent to vascular side branches or within tightly curved vessels. Inadequate filter apposition and sealing against a vessel wall has the undesirable effect of allowing emboli passage.

To ensure filter apposition and sealing against a vessel wall, without inducing undue vascular trauma, the radial force exerted by the filter against the vessel wall should be optimized. Typical methods used to increase the radial force exerted by the filter include, for example, increasing the cross-sectional area (moment of inertia and therefore the stiffness) of the filter support frame and in particular the tethering elements of the frame. Enhanced radial force can also be achieved by incorporating additional support members or by enlarging the "relaxed" or deployed diameter of the filter frame relative to the diameter of the vessel into which it is deployed. These methods typically have the undesirable side effects of degrading the longitudinal compliance, adding to the compressed delivery profile, and, in some cases, increasing the deployed length. Some methods used to increase the radial force (for example, stiffer support frames) have the additional drawback of requiring thicker-walled, larger profile, delivery catheters. To accommodate the increased pressure exerted by the stiff frame (constrained within the delivery catheter) a commensurately thicker catheter wall is required, compromising the delivery profile.

SUMMARY OF INVENTION

The present invention is an improved embolic filter frame having looped support struts. The frame configuration of the present invention provides enhanced longitudinal compliance, improved sealing against a vessel wall, low profile delivery, and a short deployed length occupied by the frame and tethering elements.

To improve the apposition and sealing against a vessel wall, the present invention incorporates a filter support frame having "looped" support struts. The "looped" strut configuration enhances the radial force imparted onto a vessel wall without entailing the undesirable side effects previously described. The looped strut configuration also facilitates filter frame opposition when deployed in tortuous vascular anatomies. When in a tensioned or compressed delivery state, the looped support struts of the present invention assume an essentially longitudinal configuration and impart minimal radial force onto the catheter wall. The thickness of the catheter wall or radial constraint can therefore be minimized to increase flexibility, decrease the catheter profile, and enhance insertion trackabilty. During the deployment procedure, the looped support struts assume a looped configuration. Once in the deployed, looped configuration, the support struts exert a high degree of radial force onto the vessel wall, enhancing apposition and sealing. The looped support struts also provide a high degree of longitudinal compliance relative to conventional designs. In addition, the full length of the looped support struts is positioned very close to the filter element, which minimizes the overall deployed length of the filter media support element.

Among the important benefits of the present invention is that the deployed device of the present invention exhibits a low degree of "longitudinal" stiffness. Thus, in the deployed state, the device remains limp and compliant in the longitudinal direction. Consequently, minor longitudinal displacements of the support wire or catheter are not translated to the filter frame and vessel wall during guide wire manipulation.

Another beneficial feature of the present invention is that the looped struts and the central collar connecting the support struts to the support wire of the present invention are positioned essentially within the plane of the filter opening and, if desired, can even be positioned within the filter frame element itself. This improves the utility of the embolic filter of the present invention by reducing the overall deployed length of the filter support frame and allowing the filter to be deployed very close to the treatment site.

These enhanced features and other attributes of the embolic filter of the present invention are better understood through review of the following specification.

BRIEF DESCRIPTION OF DRAWINGS

The operation of the present invention should become apparent from the following description when considered in conjunction with the accompanying drawings, in which:

FIGS. 8A and 8B are, respectively, an end view and a side view of one embodiment of an embolic filter of the present invention, showing three support struts with loops, as viewed along two orthogonal axes.

FIGS. 9A and 9B are, respectively, an end view and a side view of a further embodiment of an embolic filter of the present invention, showing three support struts with loops, as viewed along two orthogonal axes.

FIGS. 10A and 10B are, respectively, an end view and a side view of another embodiment of an embolic filter of the present invention, showing three support struts with loops, as viewed along two orthogonal axes.

FIGS. 11A and 11B are, respectively, an end view and a side view of still another embodiment of an embolic filter of the present invention, showing three support struts with loops, as viewed along two orthogonal axes.

DETAILED DESCRIPTION OF THE INVENTION

Figure 1:
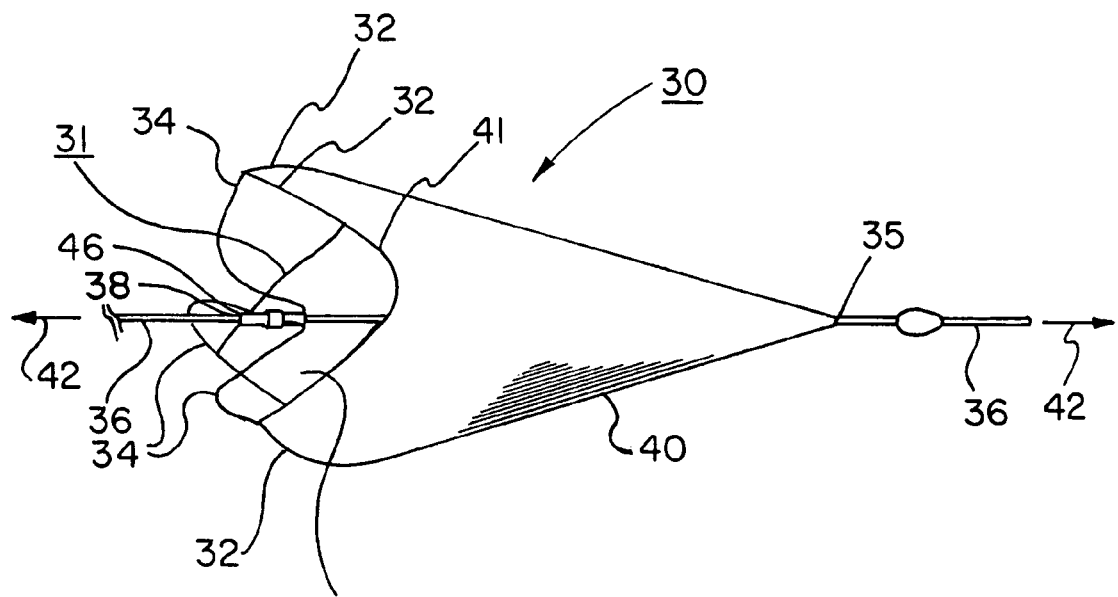
FIG. 1 is a three-quarter isometric view of an embolic filter of the present invention, with a support frame having three looped support struts.

A first embodiment of the present invention is shown in FIG. 1. Shown is an unconstrained, non-tensioned embolic filter assembly 30 of the present invention. The filter assembly 30 comprises a frame 31 having two distinct portions: a filter support portion 32 and a series of looped struts or tethers 34. Each looped strut 34 is affixed to a central collar 46, which is then attached to a support wire 36 at attachment point 38. Multiple struts 34 emanate radially outward and are attached to the frame's filter support portion 32. Attached to the filter support portion 32 is a filter element 40. Also shown is a longitudinal axis 42, which is essentially coincident with the support wire 36.

Embolic filter frames of the present invention can have 2, 3, 4, 5, 6, 7, 8 or more looped support struts. The number of support struts can effect the profile and shape of the filter membrane opening 60. For example, the frame configuration in FIG. 1, showing only three support struts for clarity, typically results in a filter opening having three "scallops" 41 which follow the profile of the filter support portion 32. By incorporating additional support struts, the magnitude or size of each scallop 41 is reduced and the filter opening will more closely approximate a circle within a plane. In a preferred embodiment, six looped support struts are incorporated into a frame of the present invention. The filter element may be trimmed to match the contour of the scallops so to avoid deflecting or disrupting fluid flow or potentially allowing inadvertent passage of emboli.

The distal end 35 of the filter element is preferably provided with a slidable attachment around the support wire 36 so as to allow the filter element to change position relative to the support wire 36 between compacted and deployed dimensions. Additionally, a slidable interface between the distal end 35 and the support element allows the filter element to remain fully extended in the vessel at all times, even when the filter assembly is undergoing longitudinal compliance, as described herein. Alternatively or additionally, the filter element may be formed from an elastic material that can accommodate different distal end positions relative to the position of the filter frame.

Figure 2:
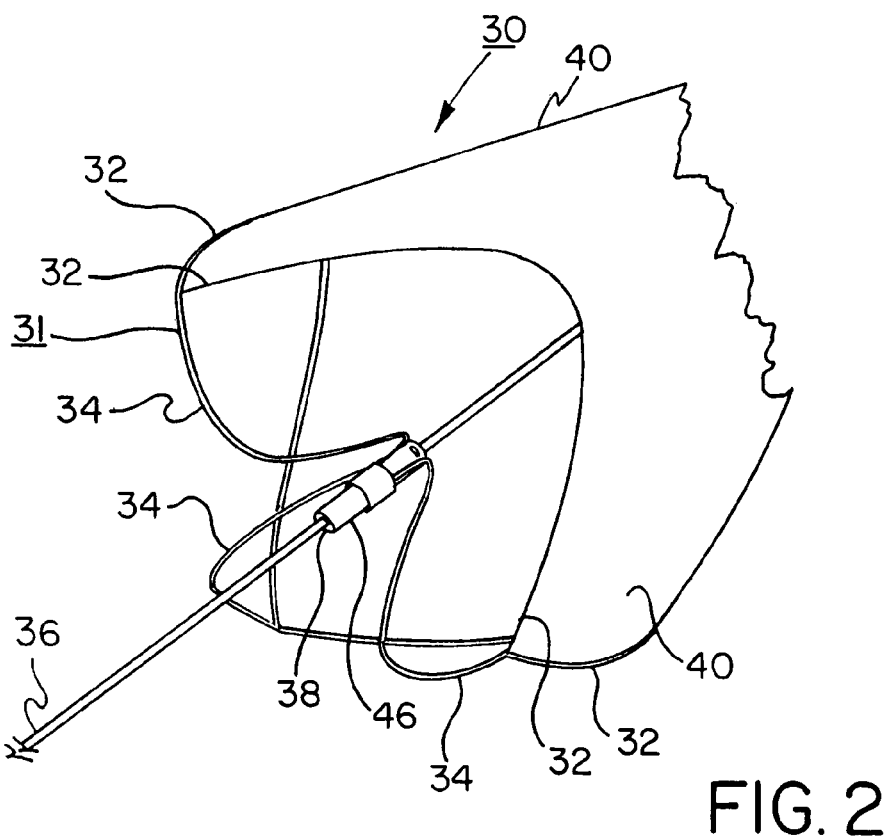
FIG. 2 is an enlarged partial view of the support frame of FIG. 1.

Shown in FIG. 2 is an enlarged view of the unconstrained looped support struts of an embolic filter 30 of the present invention. Shown is a frame 31 having filter support portions 32 and three looped support struts 34. Also shown are support wire 36, central collar 46, collar to support wire attachment point 38, and a filter element 40. Shown is a preferred embodiment in which the looped support struts 34 are essentially "s" shaped.

Figure 3A:
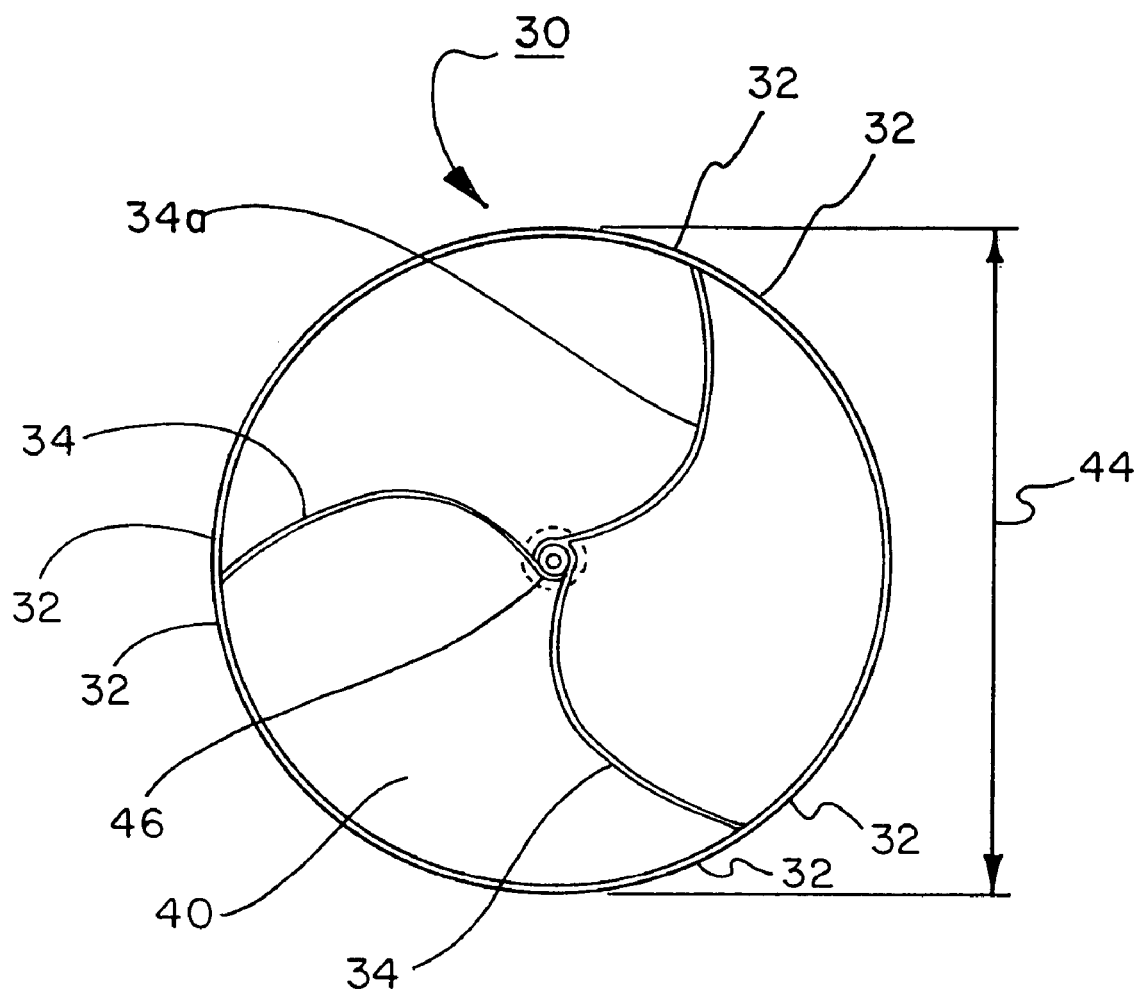
FIG. 3A is an end view of the embolic filter of FIG. 1, depicting the support frame assuming an unconstrained diameter.

FIG. 3A illustrates the unconstrained embolic filter assembly 30 from FIGS. 1 and 2. Shown are three preferred s-shaped, looped support struts 34 extending radially from the central collar 46. The support struts 34 extend from and are attached to a filter support portion 32. Attached to the filter support portion 32 is a filter element 40. The embolic filter 30, shown in an unconstrained state, has an unconstrained diameter 44.

Referring again to FIG. 2, shown are three looped support struts 34, support wire 36, central collar 46, collar to support wire attachment point 38, and a filter element 40. It will be noted that attachment point 38 may comprise a rigidly secure fixation point between the support wire 36 and the centered collar 46, or it may comprise a slideable interface between the support wire 36 and central collar 46; thereby decoupling longitudinal or rotational motion of the support wire from the filter frame. The support struts 34 extend radially and are attached to a filter support portion 32. Attached to the filter support portion 32 is a filter element 40. A "filter support portion" is defined as that portion of a filter frame that is at least partially attached to a filter element 40. A "support strut" is defined as that portion of a filter frame that supports the filter support portion and generally is not attached directly to the filter element 40.

Figure 3B:
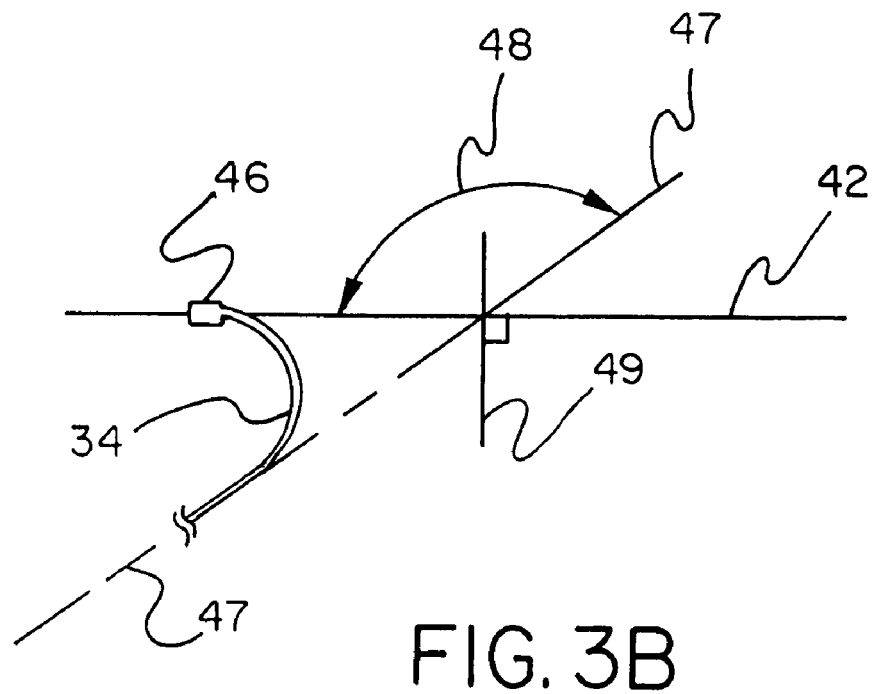
FIG. 3B is a partial side-view of a looped support strut of the present invention, defining a bend angle in the support strut.

A "looped support strut" is further illustrated in FIG. 3B. Shown is the support strut 34 unattached to a filter element and constrained about a support wire or longitudinal axis 42. A reference axis 47, drawn through the support strut 34 as shown, approximates the magnitude of a bend or loop in the support strut. The axis 47 defines an angle 48 relative to the longitudinal axis 42 (also shown is a reference axis 49 which defines a 90 degree angle relative to the longitudinal axis 42). Shown is a looped support strut angle 48, which is greater than 90 degrees, relative to the longitudinal axis 42. A "looped strut" is therefore defined as a filter frame support strut, having a portion unattached to a filter element, wherein the strut has at least one bend equal to or greater than 90 degrees along the unattached portion. The looped angle can be viewed and measured about any axis.

Figure 3C:
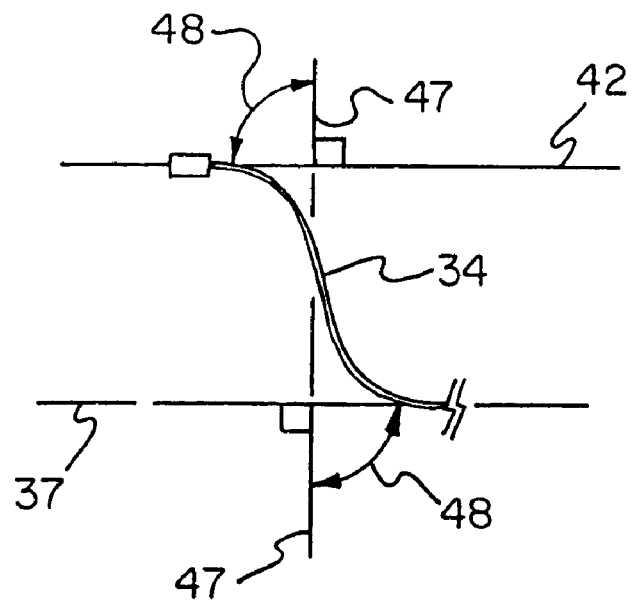
FIG. 3C is a partial side-view of a looped support strut of the present invention, defining an "s" shape in the support strut.

A looped, embolic filter frame support strut having an "s" shape is depicted in FIG. 3C. Shown is the support strut 34 unattached to a filter element and constrained about a longitudinal axis 42. Also shown is an axis 37, which is parallel to the longitudinal axis 42. A reference axis 47, drawn through the support strut 34, as shown, approximates the magnitude of the bends or loops in the support strut. The axis 47 defines angles 48 relative to the longitudinal axis 42. Shown are two opposite bend angles 48, each of at least about 90 degrees. A "support strut having an 's' shape" is defined as a filter frame support strut having a portion unattached to a filter element, wherein the strut has at least two opposite bends greater than about 90 degrees along the unattached portion. The angles 48 can be viewed and measured about any axis.

Figure 4:
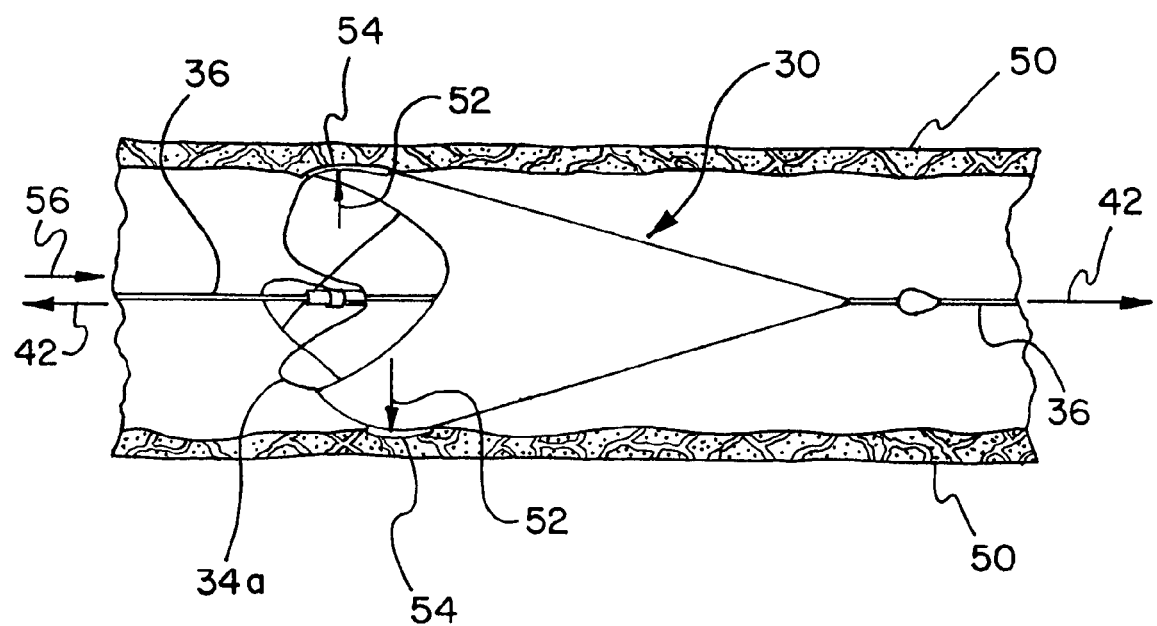
FIG. 4 is a three-quarter isometric view of an embolic filter of the present invention as deployed into a vessel.

The aspect of "longitudinal compliance" is further clarified in FIG. 4. Shown is an embolic filter assembly 30 of the present invention deployed within a compliant vessel 50 (shown in longitudinal cross-section). The vessel 50 defines an inner diameter which is slightly smaller, for example approximately 90%, than the unconstrained diameter of the device. This is shown as diameter 44 in FIG. 3A. The "undersized" vessel therefore imparts a radial constraint to the deployed filter, which prevents the filter from expanding to a full, unconstrained diameter. In this process, an interference fit between the filter and vessel wall is achieved. The looped support struts 34 when constrained by a vessel therefore exert a radial or expansive force 52 onto the vessel wall 50, forming a seal region 54. This radial, expansive force 52 can also be referred to as the "hoop stress" or "radial force" applied to the vessel wall.

As the term "unconstrained diameter" is used herein, it is intended to describe the device of the present invention as it self-deploys on a tabletop. In this form it is both unconstrained and untensioned. This state is also referred to herein as being "not in tension" or in a "non-tensioned" state.

Once deployed, the support wire 36, when rigidly fixed at or about the central collar, can be slightly displaced along the longitudinal axis 42 in directions 56 or 58 without significantly disrupting or translating to the seal region 54. The looped support struts 34 therefore provide a degree of "longitudinal compliance" which effectively isolates the filter element from small support wire displacements. Devices of the presents invention having unconstrained diameters of about 6 mm (0.24") can tolerate support wire displacements in directions 56 or 58 of about ±0.8 mm (±0.03") or more, without causing a significant disruption or translation to the seal region 54. The support wire therefore has a "maximum total displacement" before causing a disruption to the seal region 54.

Longitudinal compliance can be alternately expressed as a ratio of unconstrained diameter divided by the maximum total support wire displacement when rigidly fixed to the support wire (without disrupting or translating the seal region against the vessel wall). To determine this ratio, a device of the present invention can be deployed within a transparent elastic tube having a diameter of about 80% of the filter's unconstrained diameter. The maximum total support wire displacement (without disrupting or moving the seal region) can then be approximated. Devices of the present invention display ratios of unconstrained diameter divided by the maximum total displacement of the support wire of about 6 or less. Preferably, the embolic filter of the present invention has a ratio of unconstrained diameter to maximum support wire displacement of about 5, about 4, about 3, about 2.5, about 2, about 1.5, about 1.2, or about 1.

A relatively easy test to quantify longitudinal compliance in the present invention is to deploy the filter apparatus within a silicone tube (such as that available from JAMAK Healthcare Technologies, Weatherford, Tex.) having a thin wall thickness of approximately 0.25 mm (0.01") and having an internal diameter of approximately 80% that of the unconstrained filter apparatus. It should be noted that the use of an 80% constrained diameter is preferred since a 20% interference fit between the device and the vessel will prevent device migration and provide adequate sealing. Once deployed and at body temperature (approximately 37° C.), the support wire to which the apparatus is attached may be longitudinally manipulated. The maximum distance the support wire can be displaced (in a longitudinal direction) without moving the filter frame in relation to the silicone tubing is recorded as "longitudinal compliance."

Figure 5A:
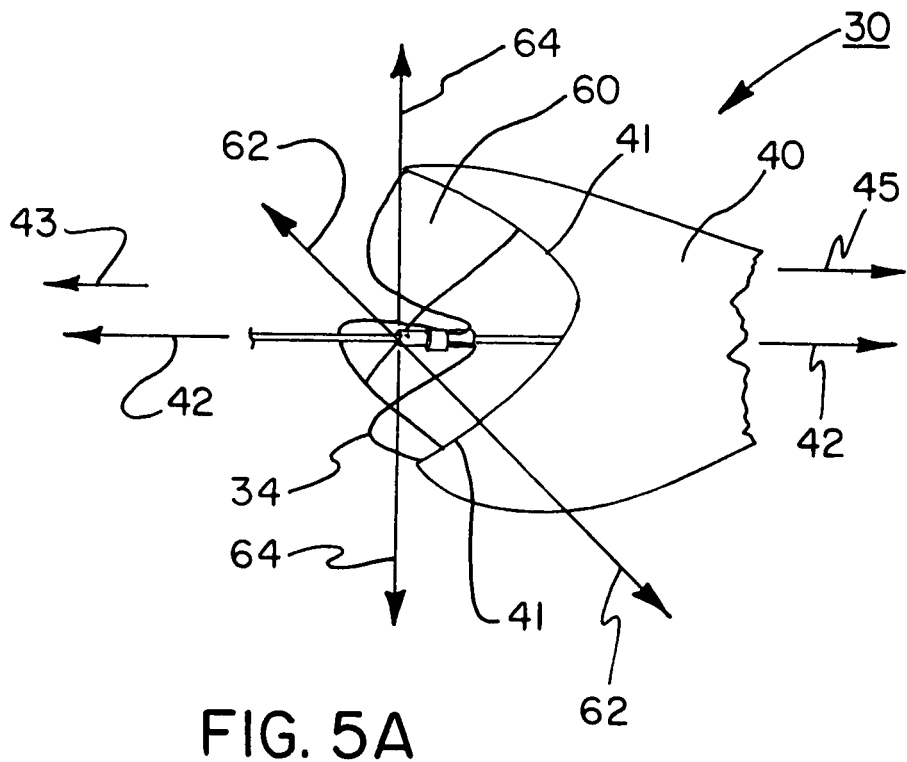
FIG. 5A is a partial three-quarter isometric view of an embolic filter of the present invention, defining the filter opening planes.

The present invention also has the beneficial feature of a short deployed length, as depicted in FIGS. 5A through 5D. The short deployed length of the present invention is a result of the looped struts and the central collar connecting the support struts to the support wire being positioned essentially within the plane of the filter opening. Depending upon the demands of particular applications, the looped struts can be engineered to deploy to be directly within the plane of the opening to the filter element, slightly upstream of the opening, or even slightly downstream of the opening so as to orient within the filter frame element itself. Shown in FIG. 5A is an embolic filter 30 of the present invention in an unconstrained state having a proximal end 43 and a distal end 45. The filter element 40 has a filter "opening" 60, which defines a plane having an x-axis 62 and an y-axis 64. For filter openings with scallops 41, the opening axis 62 and 64 are positioned at the most proximal ends of the scallops 41. The opening plane shown is orthogonal to the support wire 36 and the longitudinal axis 42. The two axes 62, 64 therefore define the plane of the filter opening 60. Looped struts 34, of the present invention are joined onto a central collar 46, which is attached to the support wire 36 at attachment point 38 via either rigidly fixed or slideable means.

Figure 5B:
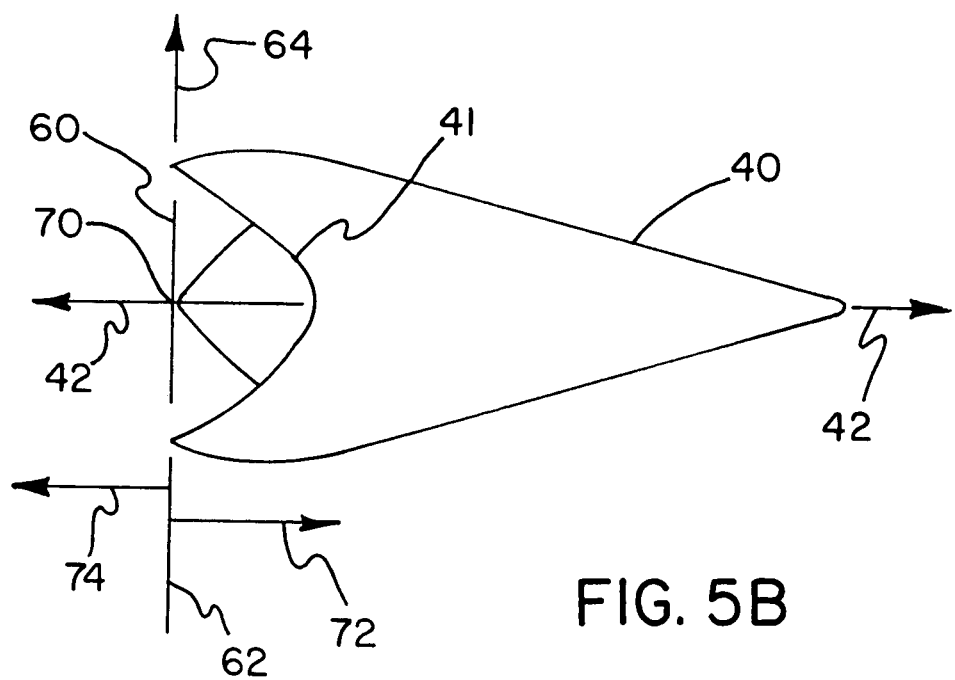
FIGS. 5B through 5D are side views of an embolic filter of the present invention illustrating deployed diameters and various types of offset strut attachment points.

Shown in FIG. 5B is a filter element 40 having a filter opening 60, an y-axis 64, and a longitudinal axis 42. The axis 64 is an "edge-view" of the plane of the filter opening. Axes 42 and 64 intersect at point 70. Point 70 is therefore on the plane of the filter opening. For clarity, a point or location on the longitudinal axis 42 is considered to be "offset distally" from the plane of the filter opening if the point lies within the filter element in the longitudinal direction labeled 72. Conversely, a point or location on the longitudinal axis 42 is considered to be "offset proximally" from the plane of the filter opening if the point lies outside of the filter element in the longitudinal direction labeled 74.

Figure 5C:
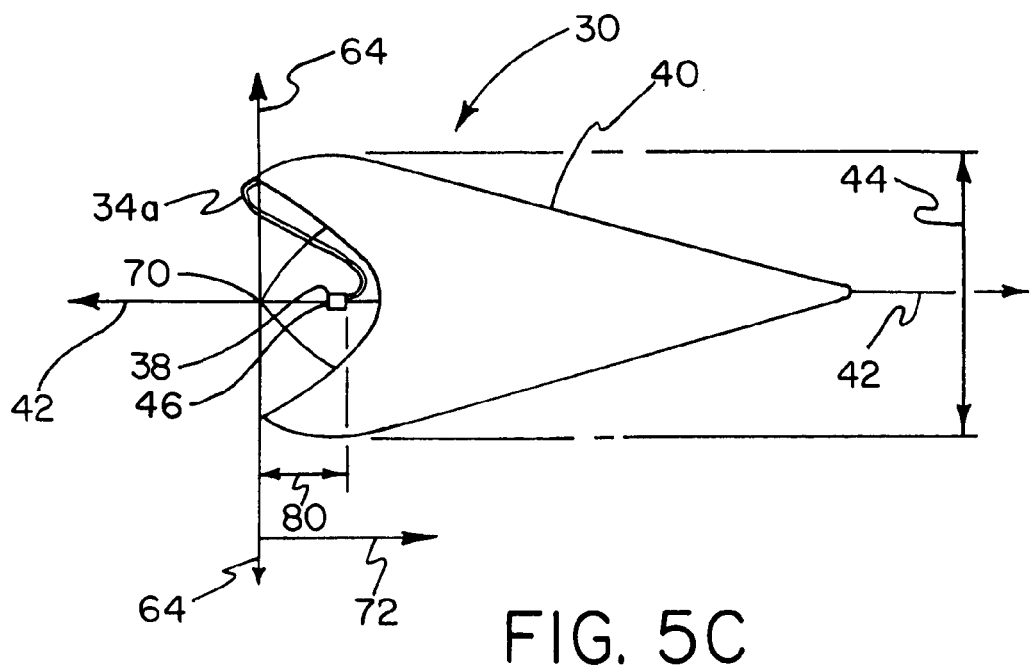

FIG. 5C illustrates a looped support strut 34 and central collar 46 of the present invention having a support wire attachment point 38 which is rigidly fixed to the support wire and off-set distally from the plane of the filter opening 64. Shown is a support wire attachment point 38 positioned inside the filter element 40 in the distal direction 72. The magnitude of the attachment point offset is shown as element 80.

Figure 5D:
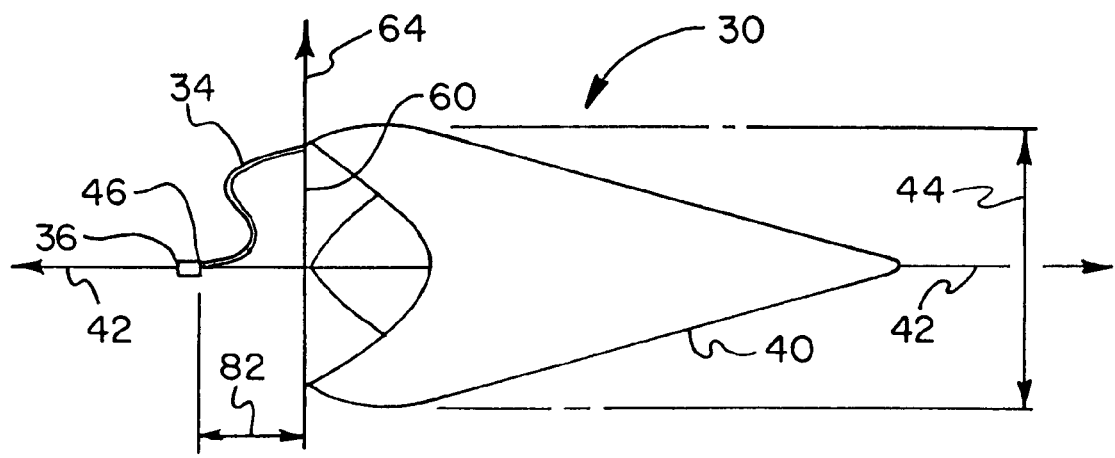

FIG. 5D illustrates a looped support strut 34 and central collar 46 of the present invention having a support wire attachment point 38 which is rigidly fixed to the support wire and off-set proximally from the plane of the filter opening 64. Shown is a support wire attachment point 38, positioned outside of the filter element 40, in the proximal direction 74. The magnitude of the attachment point offset is shown as item 82.

The relative magnitude of any off-set, along with the direction of the off-set between a support wire attachment point and the plane of the filter opening 64, can be expressed by an "offset ratio" of the strut attachment point off-set divided by the unconstrained diameter 44. For example, a filter having a strut attachment point offset of 4 mm and an unconstrained diameter of 10 mm, would have a ratio of 0.4. This ratio can be applied to strut to support wire attachment points that are offset distally or proximally to the plane of the filter opening. A ratio of "zero" would reflect no offset, or in other words an attachment point lying in the plane of the filter opening.

Embolic filters of the present invention can have distally offset ratios (of the attachment point off-set divided the unconstrained diameter) ranging from about 0 to about 1, with a preferred range of about 0 to about 0.7, with a most preferred range of about 0.2 to about 0.5. These distally offset ratios reflect strut/collar to support wire attachments positioned within the filter element. Similarly, embolic filter of the present invention can have proximally offset ratios, reflecting strut/collar to support wire attachments positioned outside of the filter element. In these configurations, embolic filters of the present invention can have offset ratios (attachment point offset divided by the unconstrained diameter) ranging from about 0 to about 1.

Devices of the present invention can be configured to have a strut to central collar attachment points that are significantly different than the central collar to support wire attachment points. For these configurations, both attachment points are then approximated by a point on the support wire that is in closest proximity to the strut.

The looped support struts of the present invention allow a short deployed length that enhances navigation within tortuous vessels and allows deployment near vascular sidebranches. To quantify as having the aspect of "short deployed length," a device should be defined by at least one of the five ratios defined below.

Figure 6A:
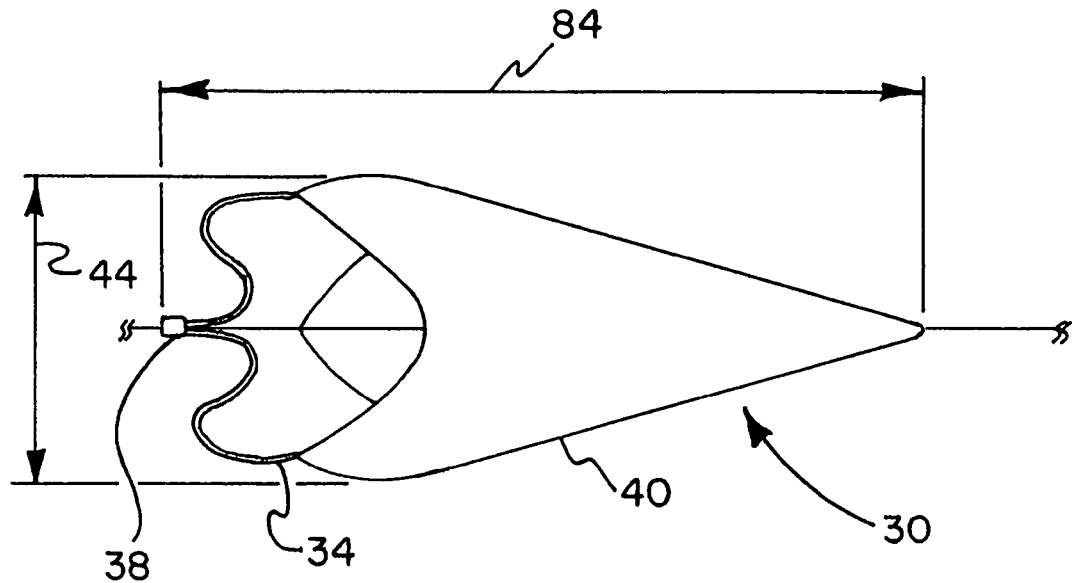
FIGS. 6A and 6B are side views of an embolic filter of the present invention defining deployed diameters and overall lengths.

The deployed length of a filter can be expressed by a first ratio of the deployed length divided by the unconstrained diameter of the filter. Shown in FIG. 6A is an embolic filter 30 of the present invention having a filter element 40, looped struts 34, strut/collar to support wire attachment point 38 (lying outside of the filter element), and a unconstrained diameter 44. Shown is a deployed length 84, which includes the looped struts 34 and the attachment point 38.

Figure 6B:
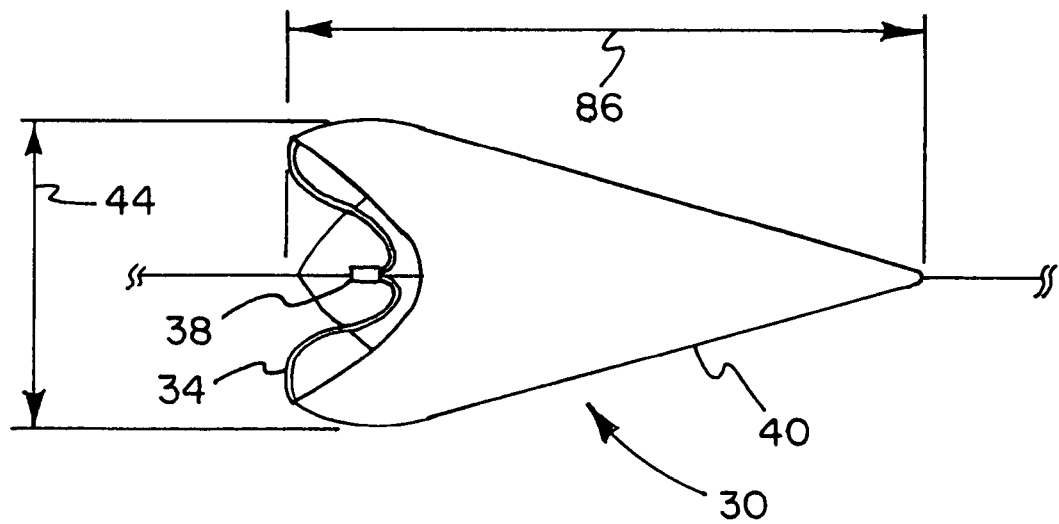

Shown in FIG. 6B is an embolic filter 30 of the present invention having a filter element 40, looped struts 34*a*, strut/collar to support wire attachment point 38 (lying within the filter element), and a unconstrained diameter 44. Shown is a deployed length 86, which is referenced from the opposing ends of the filter element, and does not include the looped struts 34*a* or the attachment point 38.

Embolic filters of the present invention can have ratios of the deployed length 84, 86 divided by the filter unconstrained diameter 44, ranging from about 0.5 to about 7, with a preferred range of about 1 to about 5, with a most preferred range of about 2 to about 4.

Figure 6C:
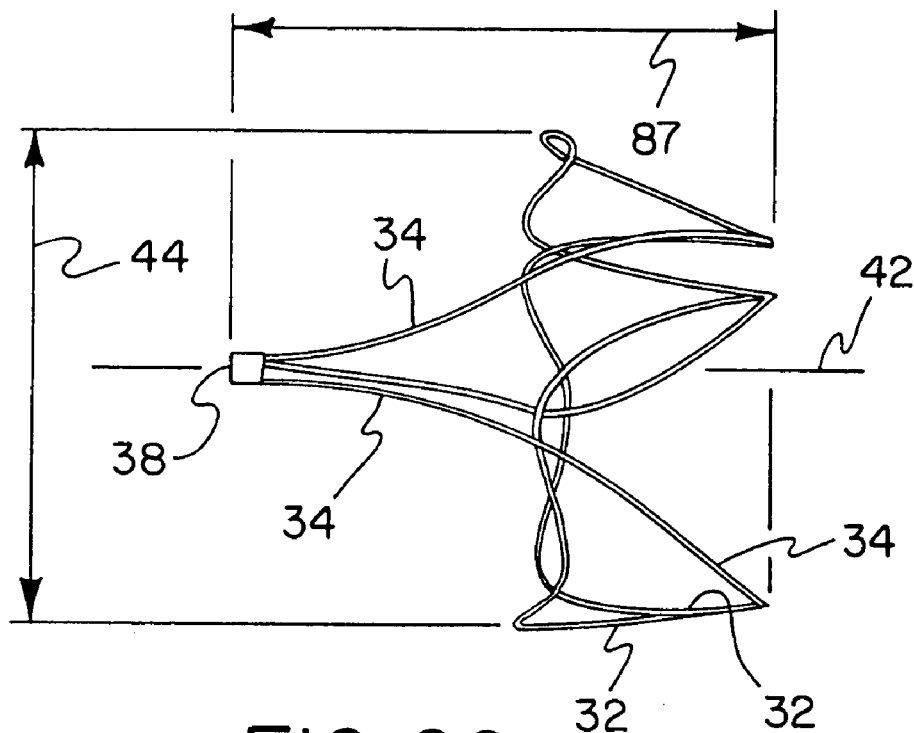
FIGS. 6C and 6D are side views of an embolic filter frame of the present invention, defining deployed diameters and lengths.

A similar expression of a filter deployed length or footprint is a second ratio of the deployed length of the frame (not including a filter element) divided by the frame unconstrained diameter. Shown in FIG. 6C is an embolic filter frame of the present invention having filter support portions 32 and looped struts 34, strut/collar to support wire attachment point 38 (lying outside of the filter element 40), and a unconstrained frame diameter 44. Shown is a frame deployed length 87, which does not include the filter element 40.

Figure 6D:
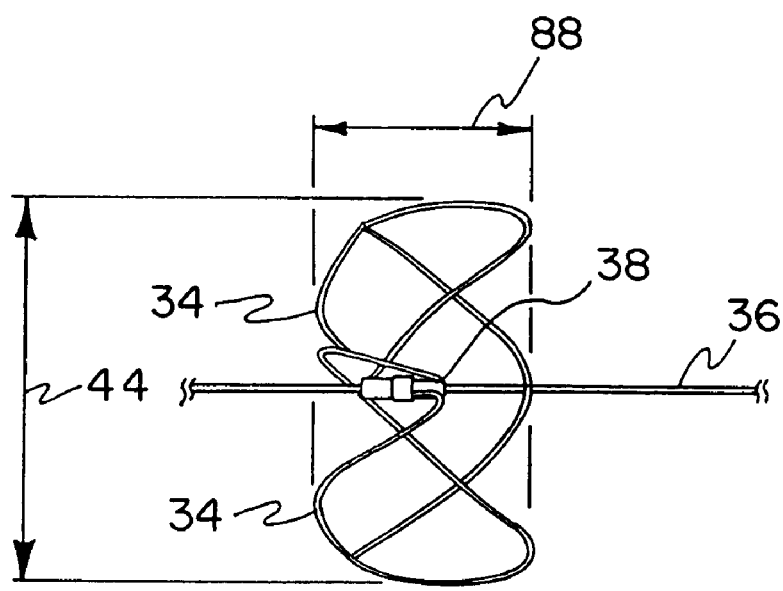

Shown in FIG. 6D is an embolic filter frame of the present invention having filter support portions 32 and looped struts 34, strut/collar to support wire attachment point 38 (lying within the filter element 40), and a unconstrained diameter 44. Shown is a frame deployed length 88, which does not include the filter element 40.

Embolic filters of the present invention can have ratios of the frame deployed length 87, 88 divided by the frame unconstrained diameter 44, ranging from about 0.1 to about 7, with a preferred range of about 0.3 to about 2, with a most preferred range of about 0.5 to about 1.

Additional benefits of the looped struts of the present invention relate to the delivery aspects of the embolic filter as shown in FIGS. 7A through 7D. The looped support struts of the present invention when tensioned elongate and assume a compacted and essentially linear form. While constrained in this linear state by a delivery catheter or other constraint means, the support struts exert relatively little force onto the radial constraint means, which permits the radial constraint means to be very thin and/or delicate. The overall delivery profile and stiffness are therefore reduced over those required for prior embolic filter devices. When the delivery catheter constraint is removed during deployment, the struts of the present invention spontaneously open and assume a looped configuration, which exert a high degree of force onto the vessel wall, creating an enhanced filter to vessel wall seal.

Figure 7A:
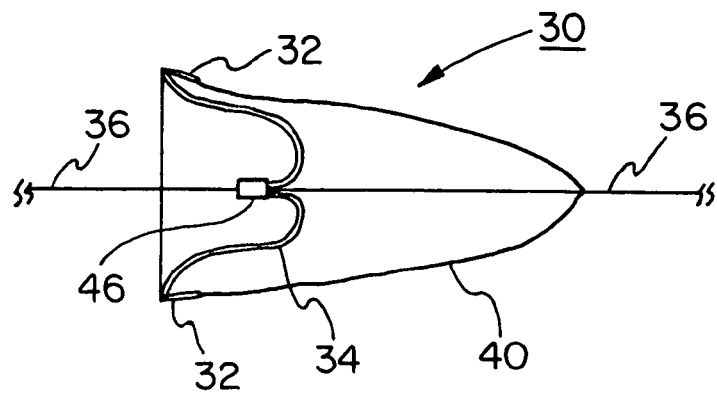
FIGS. 7A through 7C are side views of an embolic filter of the present invention, showing various stages of tensioning and elongation.

Shown in FIG. 7A is an embolic filter 30 of the present invention having looped struts 34 attached to a central collar 46. The central collar is attached to a support wire 36. The support struts emanate radially outward and are integral to (or joined to) a frame having a filter support portion 32. A filter element 40 is attached to the filter support portion 32.

Figure 7B:
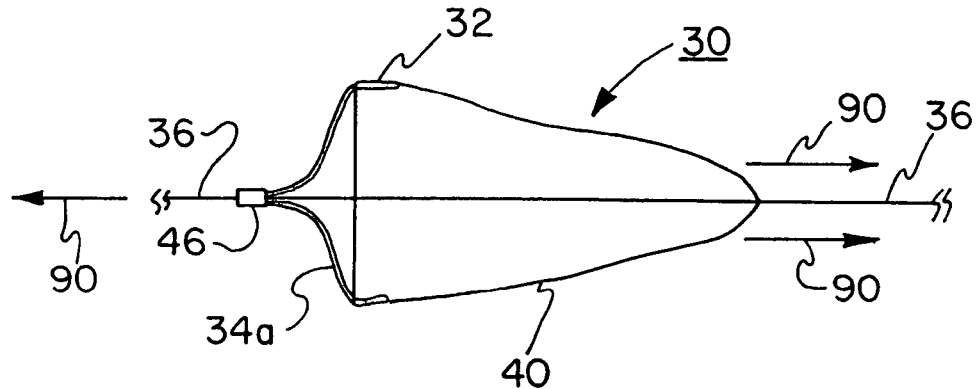
Figure 7C:
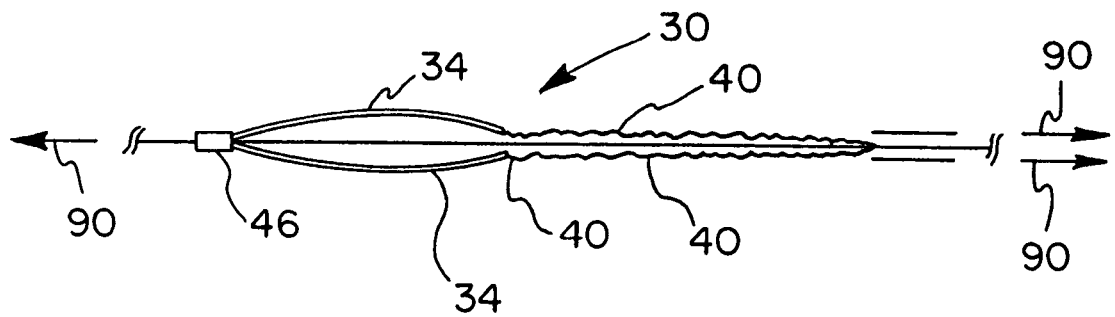
Figure 7D:
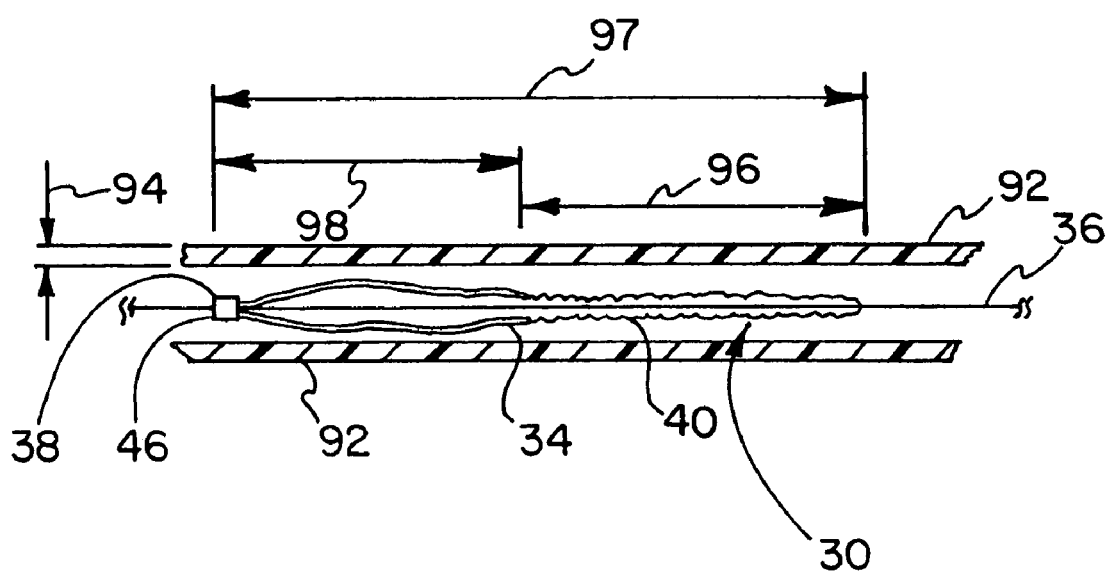
FIG. 7D is a side view of an embolic filter of the present invention constrained within a sheath.

When tension 90 is applied to the support wire 36 and filter element 40, the looped struts 34 elastically deform to the configuration shown in FIG. 7B. As further tension 90 is applied, the embolic filter 30 and the looped struts 34 continue to elongate until the looped struts assume an essentially linear or straight form as shown in FIG. 7C. While in this elongated state, the embolic filter 30 can be inserted into a delivery catheter or withdrawn into a sheath. Shown in FIG. 7D is an elongated embolic filter 30 of the present invention having looped struts 34 in an essentially linear configuration constrained in a deliver catheter 92. The low force applied to the delivery catheter by the elongated looped strut facilitates use of a relatively thin catheter wall 94. When the constraining delivery catheter is removed during filter deployment, the looped struts of the present invention spontaneously open and assume the configuration shown in FIGS. 4 and 7A, either spontaneously or through manipulation of the support wire and/or delivery catheter.

During delivery within a vessel, struts 34 of an embolic filter of the present invention are constrained in an "essentially linear" form, as shown in FIG. 7D. While in this essentially linear form, the central support collar 46 (or strut to support wire attachment point 38) is positioned outside of the filter element 40. The central support collar 46 is also separated from the filter element 40 by the elongated and essentially linear support struts 34. Once properly deployed, however, the central support collar 46 (or strut to support wire attachment point 38) lies within the filter element 40, as shown in FIG. 7A. The central support collar 46 (or strut to support wire attachment point 38) therefore moves or translates relative to the filter element during deployment. Typical filters of the present invention undergo a relative translation (support collar to filter element) equal to at least ½ of the length of the constrained filter element 96 (as is shown in FIG. 7D).

Also shown in FIG. 7D is a total constrained delivery length 97 of an embolic filter of the present invention. Embolic filters of the present invention can have a third ratio of the total constrained delivery length 97 divided by the unconstrained length. For the present invention, this third ratio may be about 1, about 2, about 2.5, about 3, about 3.5, or greater. The unconstrained length is defined by length 84 (FIG. 6A) or by length 86 (FIG. 6B).

Similarly, embolic filters of the present invention can have a fourth ratio of the total constrained frame delivery length 98 divided by the unconstrained frame length. For the present invention, this fourth ratio may be about 2, about 2.5, about 3, about 3.5, or greater. The unconstrained frame length is defined by length 87 (FIG. 6C) or by length 88 (FIG. 6D).

A fifth ratio relating to the short deployed length is the strut constrained delivery length divided by the strut unconstrained deployed length. The strut constrained delivery length is defined as the length of a strut portion 34 of the frame, not including the filter support portion 32, as shown in FIG. 7D. The strut constrained delivery length is therefore a portion of the total frame length 98 in FIG. 7D. The strut unconstrained length is defined as the length of a unconstrained strut 34a as shown in FIGS. 6C and 6D, not including the length of a filter support portion 32. Filter frames of the present invention can have ratios of the strut constrained delivery length divided by the strut unconstrained deployed length of about 2, of about 3, of about 4, of about 5, of about 6, or about 7, or more. Filter frames of the present invention preferably have ratios of the strut constrained delivery length divided by the strut unconstrained deployed length of about 3, of about 3.5, of about 4, of about 4.5, or about 5 or more. Most preferred ratios of strut constrained delivery length divided by the strut unconstrained deployed length are about 3, about 3.3, of about 3.6, or about 4, or more.

Embolic filters of the present invention can be produced using a variety of common methods and processes. For example, an embolic filter frame with looped struts can be fabricated from any biocompatible material having adequate resilience and stiffness. For example, nitinol, stainless steel, titanium, and polymers may be employed as applicable materials. A precursor frame having looped struts may be fabricated in a planar sheet form and rolled and attached to itself to form a frame of the present invention. Alternately, a cylindrical tube can be cut and expanded or cut and compressed to form a frame of the present invention. Cutting processes can include lasers, stampings, etching, mill-cutting, water-jets, electrical discharge machining, or any other suitable process.

Filter elements or members, used in conjunction with the looped struts of the present invention, can be produced using a variety of common materials, methods and processes. Suitable biocompatible materials include, but are not limited to, metallic foilsor meshes, or sheets or meshes formed from various polymers, including fluoropolymers such as polytetrafluoroethylene. Filter members can be molded, cast, formed, or otherwise fabricated by joining various suitable materials.

FIGS. 8 through 12 illustrate (but do not limit) various alternate embodiments of looped struts of the present invention. Shown in FIGS. 8A and 8B is an embolic filter 30 having a preferred looped strut configuration 34. A preferred strut 34 of the present invention can have a looped shape or profile when viewed along two orthogonal axes. The struts 34 therefore project a looped configuration in two orthogonal views.

Alternate strut configurations of the present invention can have looped shapes when viewed along different combinations of axes or along a single axis. For example, shown in FIGS. 9A and 9B are similar views to those of 8A and 8B, showing an alternate looped strut configuration wherein the alternate strut 34 has an essentially looped shape only when viewed along a single axis. Shown is a strut 34 having a looped shape in an end view (FIG. 9A) and an essentially linear shape in a side view (FIG. 9B).

Alternately, a strut of the present invention can have an essentially linear shape when viewed on end, while having a looped shape when viewed, for example from the side. This configuration is illustrated in FIGS. 10A and 10B, which show an alternate strut 34 having an essentially linear shape when viewed from the end (FIG. 10A), while having a looped configuration when viewed from the side (FIG. 10B).

Looped support struts of the present invention can be configured with bends greater than about 90 degrees (as defined by FIG. 3C), greater than about 120 degrees, greater than about 180 degrees, greater than about 240 degrees, or more. For example, a looped strut of the present invention having a bend greater than about 200 degrees is depicted in FIG. 11A. Shown is an embolic filter 30 having looped support struts 34 with "spiral" bends of about 200 degrees or more. The struts 34 also have a looped configuration when viewed from another axis, in this case a side view, as shown in FIG. 11B. Looped support struts of the present invention can therefore have different "loop" configurations when projected onto different viewing planes.

Shown in all FIGS. 8 through 11 are embolic filters having three, looped support struts with support wire attachment points 38 and central support collars 46, lying essentially within the filter element, as previously described in FIGS. 5A and 5B. Embolic filter frames of the present invention can have 2, 3, 4, 5, 6, 7, 8, or more looped support struts. Various multiple strut configurations are depicted in FIGS. 12A through 12F.

Figure 12A:
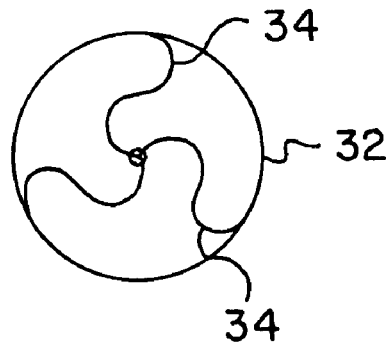
FIGS. 12A through 12F are end views of embolic filters embodiments of the present invention, showing, respectively, three, four, five, six, seven, and eight looped support struts.

FIG. 12A shows an end view of an embolic filter of the present invention having 3 looped struts 34.

Figure 12B:
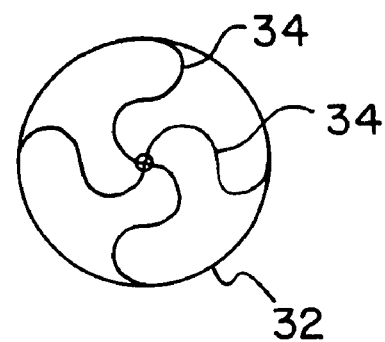

FIG. 12B shows an end view of an embolic filter of the present invention having 4 looped struts 34.

Figure 12C:
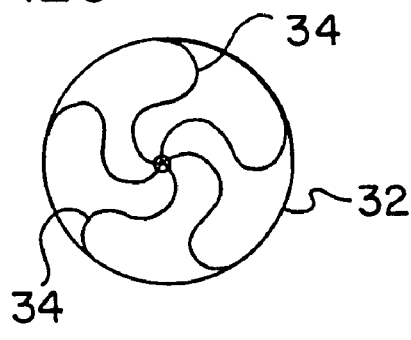

FIG. 12C shows an end view of an embolic filter of the present invention having 5 looped struts 34.

Figure 12D:
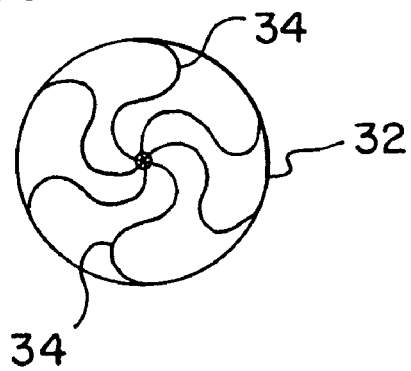

FIG. 12D shows an end view of an embolic filter of the present invention having 6 looped struts 34.

Figure 12E:
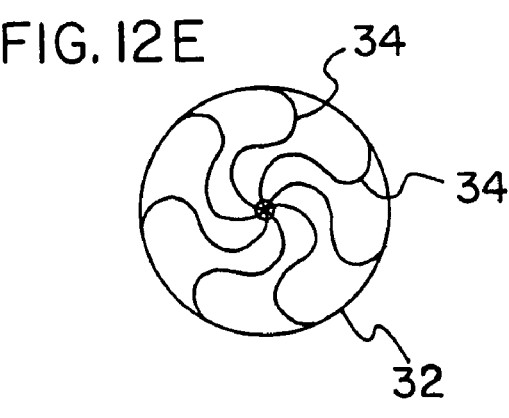

FIG. 12E shows an end view of an embolic filter of the present invention having 7 looped struts 34.

Figure 12F:
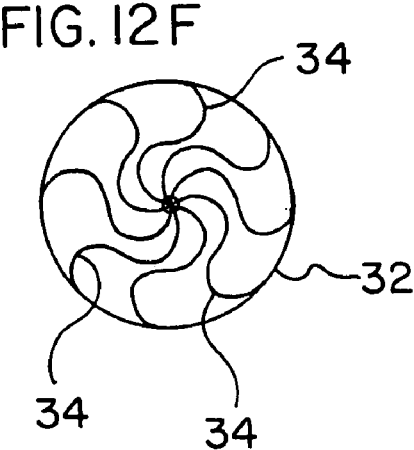

FIG. 12F shows an end view of an embolic filter of the present invention having 8 looped struts 34.

Figure 13:
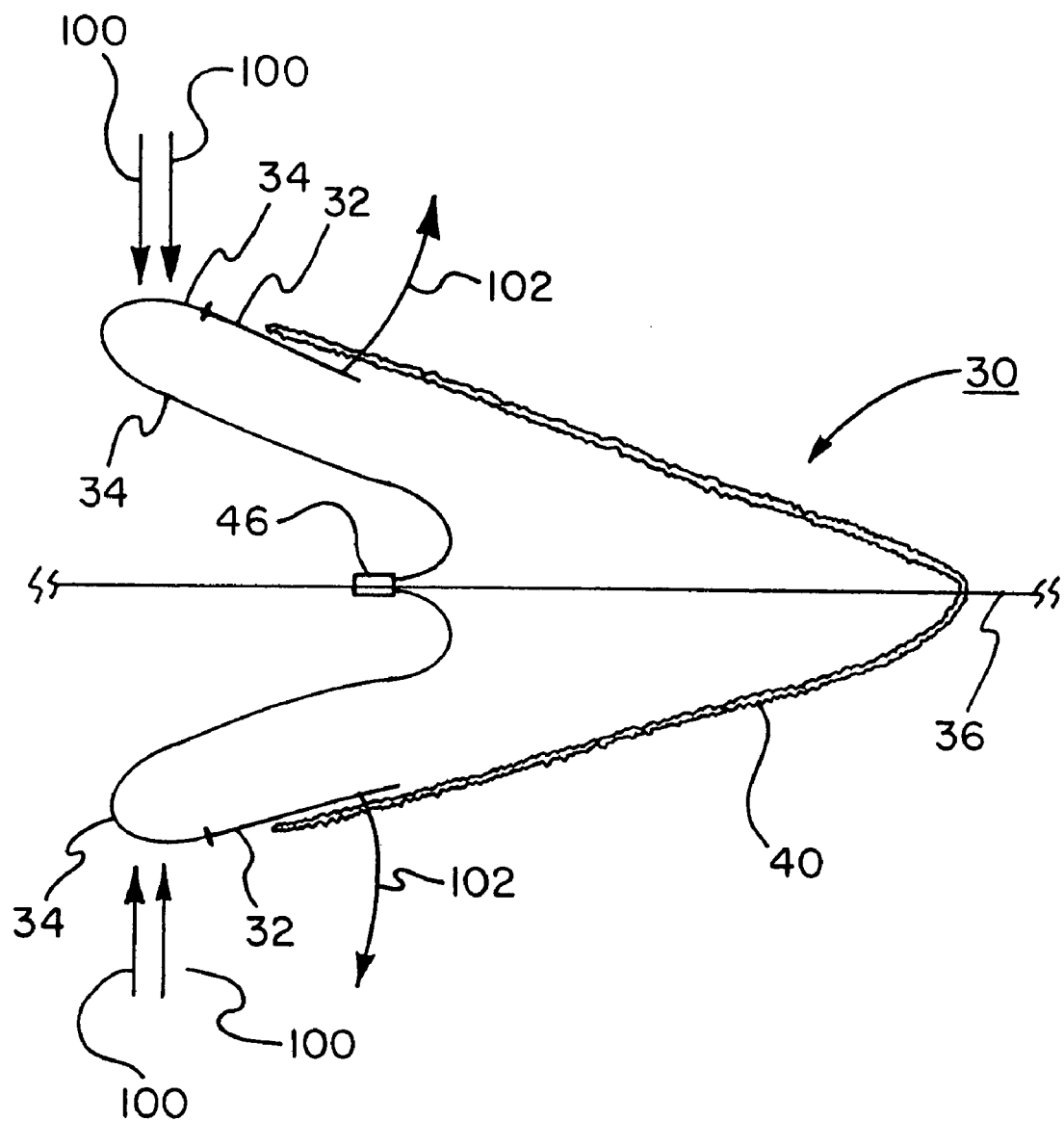
FIG. 13 is a longitudinal cross-section view of an embolic filter frame of the present invention, depicting an enhanced radial force caused by vessel wall compression.

An additional functional aspect of embolic filter frames of the present invention is shown in FIG. 13. Shown is an embolic filter 30 having looped support struts 34, filter element 40 attached to the filter element support 32, central collar 46, and support wire 36. When deployed within an undersized vessel (that is, a vessel that is undersized relative to the filter's relaxed fully deployed diameter), a compressive load 100 is applied to the frame, which counteracts the radial force applied by the frame to the vessel. The compressive load 100 causes a frame portion, in this case the filter element support portion 32, to deflect outwardly, as shown by item 102. The deflection 102 can improve the sealing between the filter element 40 and the vessel wall, further reducing the advertent passage of emboli. The additional loading onto the vessel wall can also reduce the possibility of "vascular trauma" caused by relative motion between the filter and the vessel, and opposition when deployed in curved vascular segments.

Figure 14:
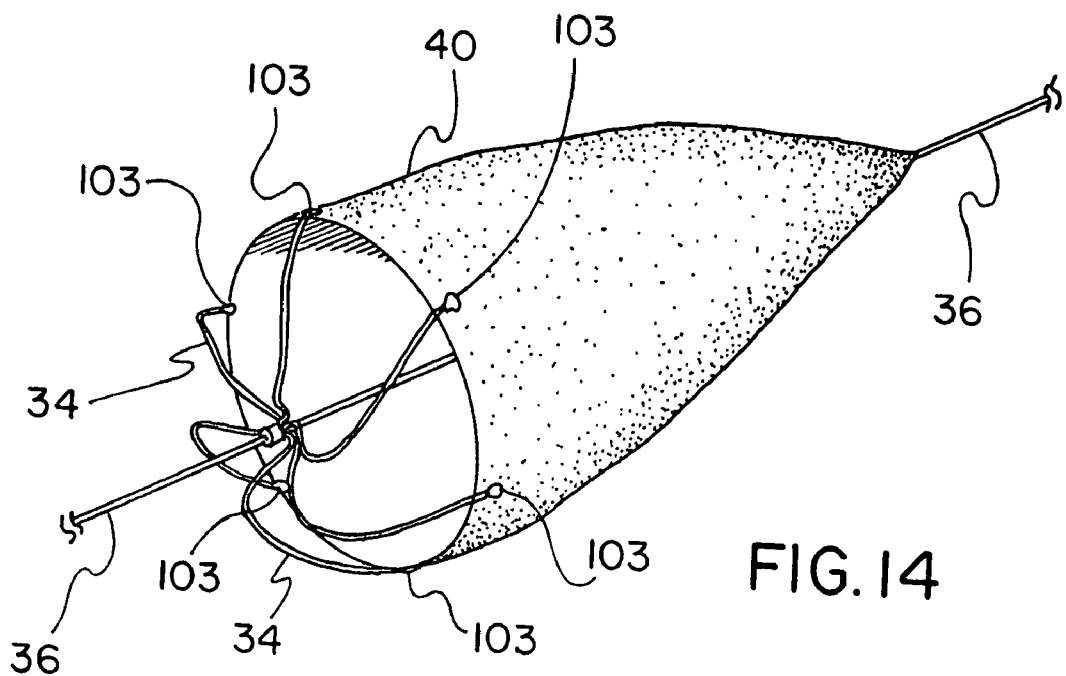
FIG. 14 is a side view of an embolic filter device of the present invention wherein the frame includes a truncated filter membrane support portion.

Shown in FIG. 14 is an alternate configuration of a frame having looped struts 34 and having a simplified filter support portion (in contrast to the elongated filter support portions 32 shown in FIG. 2). Shown are a support wire 36 and a filter element 40 attached directly to the ends of the six looped support struts 34 of the present invention. The support struts 34 attach to the filter element 40 at attachment points 103. It should be appreciated that the length and shape of the struts 34 in this embodiment may be varied to accommodate bonding of struts 34 to different points on the filter element or to bond the filter element 40 along a partial length of the struts 34.

An additional feature of a filter frame of the present invention relates to the looped strut "spontaneous" transformation from a constrained linear state to a "locked" and inverted state, similar to that of "locking pliers" or an "off-center locking clamp". Once inverted, the looped struts maintain a stable, short length, looped configuration and must be tensioned to revert back to the constrained linear state.

The term "support wire", as referred to and relating to the present invention, (for example, element 36 in FIG. 1) can include a solid or hollow support wire or can include any other tubular article with at least one continuous lumen running therethrough. A suitable support wire for use with the present invention may include, but is not limited to, a guide wire.

Filters of the present invention can be configured for deployment within a variety of articles, including, but not limited to, filtering applications within animal vessels, catheters, pipes, ducts, fluid conduits, tubes, hoses, material transfer conduits, storage containers, pumps, valves and other fluid containers. Filterable fluids include gasses, liquids, plasma and flowable solids or particulate mixtures. Fluids can flow across the filters of the present invention, or the filters can be dragged or otherwise transported through a fluid. Filters of the present invention are not limited to generally circular profiles (when viewed on end) and can have, when deployed an oval, triangular, square, polygon, or other profile. Filters of the present invention can also be combined, "ganged," or used in conjunction with other devices such as diagnostic, visualization, therapeutic instruments, or other filters. The strut configurations of the present invention can also be incorporated into non-filtering devices, such as vessel occluders, indwelling diagnostic instruments, therapeutic instruments, or visualization devices.

Without intending to limit the scope of the present invention, the device and the method of production of the present invention may be better understood by referring to the following example.

Example 1

Figure 15:
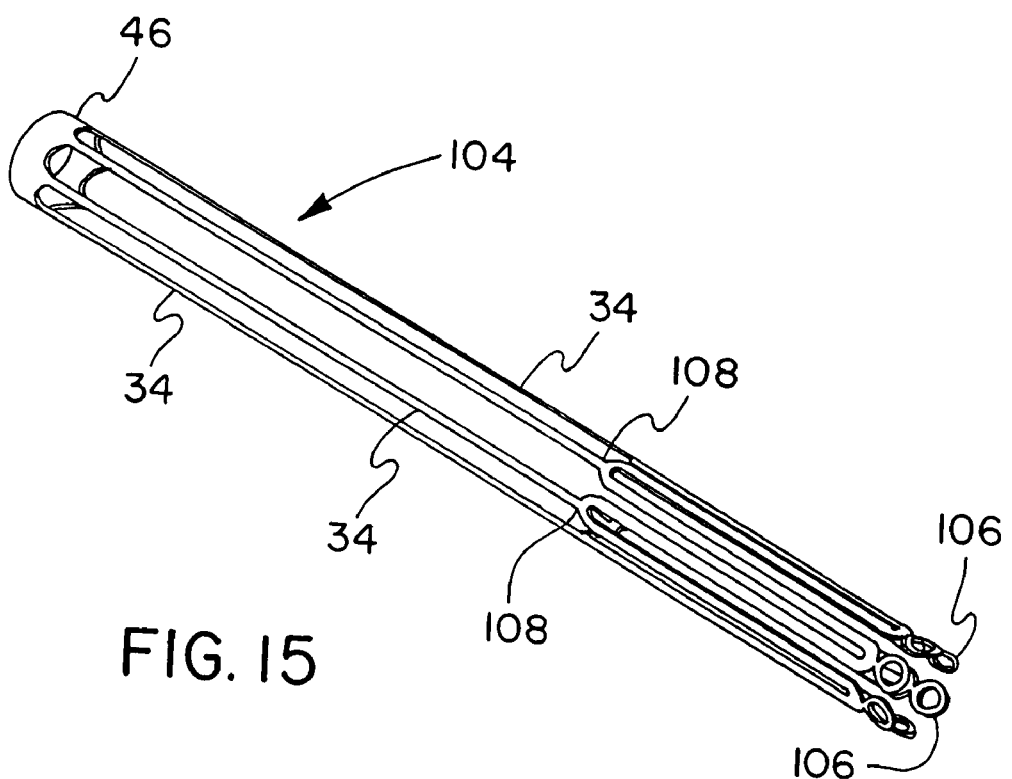
FIG. 15 is a three-quarter isometric view of a cut-out precursor tube used to fabricate a six-strut embolic filter frame of the present invention according to Example 1.

As shown in FIG. 15, a 0.9 mm nitinol tube 104, with a wall thickness of approximately 0.09 mm (obtained from SMA Inc, San Jose, Calif.) was laser cut by Laserage Technologies Inc, Waukegan, Ill., to form a frame configuration of a single, undulating, integral, 6 apex ring. The frame included radiopaque marker housings 106 at each distal apex and tether or strut elements 34 extending from each proximal apex 108 and converging at the opposite end in a "collar" 46 of uncut parent material. This frame was then lightly grit blasted at 30 psi with 20-micron silicon carbide media in a grit blasting machine (Model MB1000 available from Comco Inc, Burbank, Calif.). The frame was then gently slid up a tapered mandrel until it achieved a functional size of approximately 6 mm.

The frame and mandrel were then subjected to an initial thermal treatment to set the geometry in an initial, tapered (conical) configuration in an air convection oven (Carbolite Corporation, Sheffield, England). The frame was quenched in ambient temperature water and removed from the mandrel, resulting in a non-inverted frame.

Figure 16:
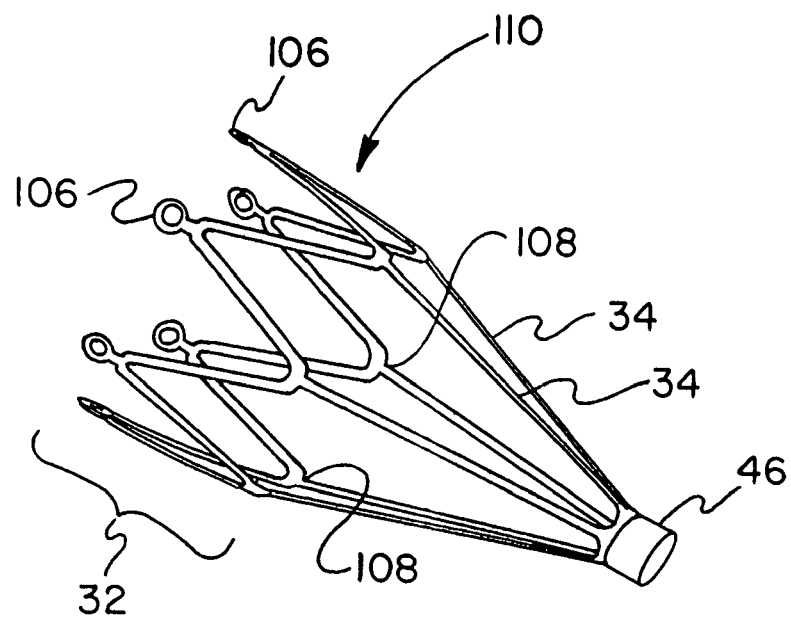
FIG. 16 is a three-quarter isometric view of the precursor tube of FIG. 15 that has been expanded to form a six-strut embolic filter frame of the present invention.

Shown in FIG. 16 is the non-inverted frame 110 having support struts 34, a central collar 46, apexes 108, and radiopaque marker housings 106. The frame portion distal to the apexes 108 form a filter element support portion 32. The frame was then placed on a second mandrel, designed to constrain the outside of the frame while allowing the inversion of the tether elements back upon themselves. Once constrained in the proper configuration, the tooling and frame were subjected to a second thermal treatment to set the final frame geometry and to set the nitinol transition to an appropriate temperature. The resulting inverted frame is depicted in FIG. 17.

Figure 17:
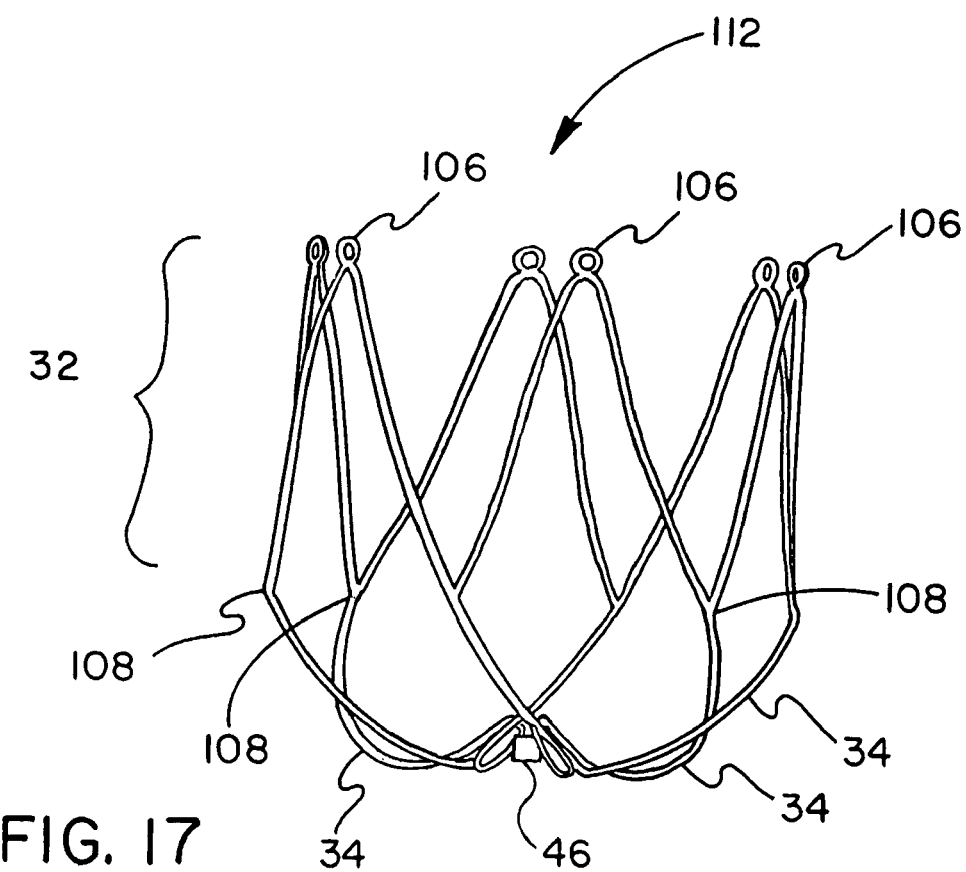
FIG. 17 is a side view of an expanded and inverted precursor tube used to fabricate a six-strut embolic filter frame of the present invention according to Example 1.

Shown in FIG. 17 is an inverted frame 112 having six looped support struts 34a, apexes 108, radiopaque housings 106, and an integral central collar 46. The frame portion distal to the apexes 108 form a filter element support portion 32.

One skilled in the art will appreciate that variances in the filter frame material(s), dimensions, geometry, and/or processing can all be made to create alternate embodiments with varying desirable properties. For example, the relative position of the central collar 46 to the apexes 108 can be varied according to FIGS. 5C and 5D.

The frame (now at functional size and preferred geometry) was then lightly coated with fluorinated ethylene propylene (FEP) powder (e.g., FEP 5101, available from DuPont Corp, Wilmington, Del.) by first stirring the powder in a kitchen blender (Hamilton Beach Blendmaster) after the powder was mixed into a "cloud," the frame was lowered into the blender for approximately 5 seconds (enough time for FEP to build up onto the surface of the frame). The frame, coated with FEP powder, was placed in an air convection oven (Grieve Oven, The Grieve Corporation, Round Lake, Ill.) set at 320° C. for approximately one minute followed by air cooling to room temperature.

A typical filtering media was made by laser perforating one layer of a thin, polytetrafluoroethylene (PTFE) membrane using a 10-watt $CO_2$ laser. The membrane thickness measured about 0.0002" (0.005 mm) and had tensile strengths of about 49,000 psi (about 340 KPa) in a first direction and of about 17,000 psi (about 120 KPa) in a second direction (perpendicular to the first direction). The tensile measurements were performed at 200 mm/min. load rate with a 1" (2.5 cm) jaw spacing. The membrane had a density of about 2.14 g/cm$^3$. The laser power and shutter time parameters were adjusted to allow the laser to consistently create uniform 0.004" (0.1 mm) diameter holes in the membrane. The hole pattern geometry was then adjusted to create a pattern with uniform hole size, uniform hole spacing, and uniform strength throughout the pattern. This perforated pattern was then folded on itself and heat-sealed using a local heat source (Weber soldering iron, EC2002M, (available through McMaster Carr, Santa Fe Springs, Calif.)) into a pattern which would result in a conical shape. The conical flat pattern was then trimmed with scissors, inverted, and mounted upon the FEP powder coated NiTi frame and attached though the application of localized heat (the heat causing the FEP coating on the frame to re-melt and flow onto the surface of the filter sack thus providing a biocompatable thermoplastic adhesive).

A guide wire component was then inserted into the collar end of the frame and a small amount of instant adhesive (Loctite 401, Loctitie Corp, Rocky Hill, Conn.) was applied and dried to adhere and create a smooth transition from the guide wire to the outer diameter (OD) of the frame collar. One skilled in the art will realize that attachment of the filter to the guide wire could be accomplished by adhesion, welding, soldering, brazing, a combination of these, or a number of other methods.

The resulting embolic filter is as shown and described above with respect to FIG. 1 et seq.

Figure 18A:
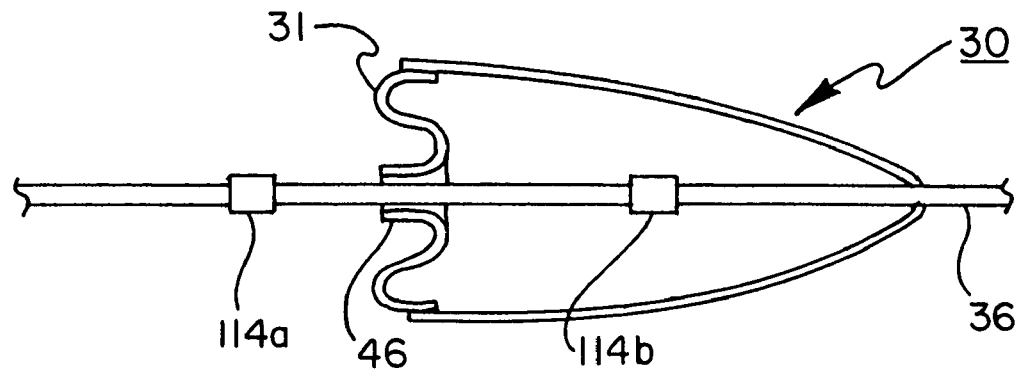
FIGS. 18A through 18C are longitudinal cross-section views of another embodiment of an embolic filter device of the present invention having a slidable attachment between the filter frame and the support wire.
Figure 18B:
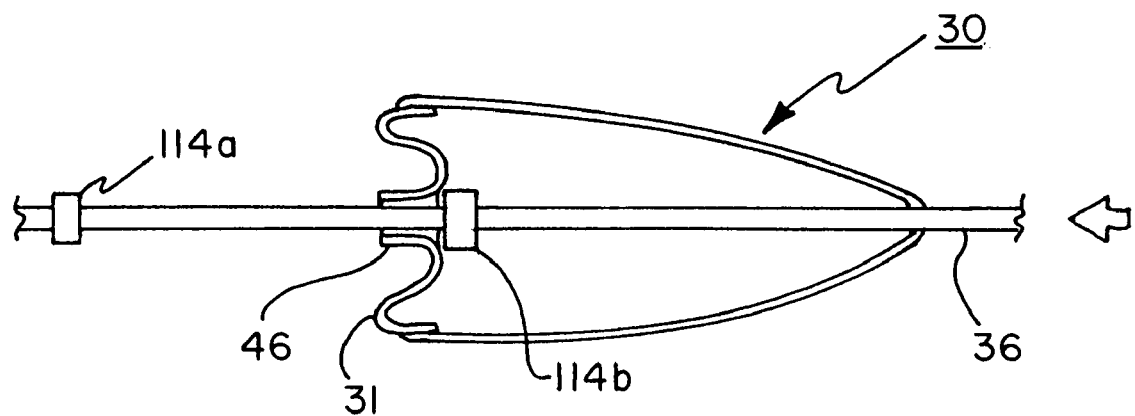
Figure 18C:
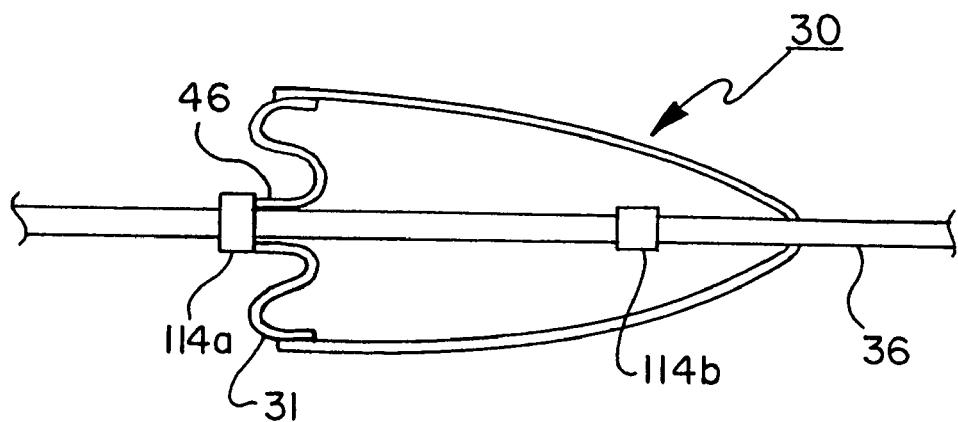

A further embodiment of the present invention is illustrated in FIGS. 18A through 18C. In this embodiment the filter assembly 30 includes a frame 31 that is slidably mounted to the support wire 36. This attachment may be accomplished through a variety of means, including by providing a collar 46 that is sized slightly larger than the support wire 36 to allow the collar to move relative to the support wire when in use. Stops 114a, 114b are provided on the support wire 36 to limit the range of relative movement between the filter assembly 30 and the support wire 36. Constructed in this manner, the filter assembly 30 has exceptional longitudinal compliance relative to the support wire in that the support wire can freely move between the stops 114 without translating longitudinal or rotational movement to the filter assembly. The full range of proximal and distal movement of the filter assembly 30 relative to the stops 114 is shown in FIGS. 18B and 18C.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. An embolic filter comprising:
   a support wire;
   an embolic filter frame having a filter support portion which is circumferentially disposed about the support wire and multiple support struts, each of the multiple support struts affixed to a collar and mounted to the support wire via the collar;
   the support struts extending radially from the support wire;
   at least one support strut having a looped configuration when not in tension in a deployed state;
   the at least one support strut positioned essentially within a plane of an opening of the filter when in the non-tensioned state; and
   a filter element attached to the filter support portion.

2. The embolic filter of claim 1 wherein the multiple support struts have looped configurations.

3. The embolic filter of claim 1 wherein at least one support strut projects a looped configuration in two orthogonal views.

4. The embolic filter of claim 1 wherein at least one support strut has an "s" shape.

5. An embolic filter comprising:
   a support wire;
   an embolic filter frame including multiple support struts that are affixed to a collar and mounted to the support wire via the collar, the multiple support struts extending radially from the support wire;
   the struts having a constrained delivery state and a non-tensioned deployed state wherein the struts in the constrained delivery state have an essentially linear form;
   at least one strut having a loop configuration when in the non-tensioned deployed state;
   the at least one strut positioned essentially within a plane of an opening of the filter when in the non-tensioned state; and
   a filter element attached to the frame.

6. The embolic filter of claim 5 further comprising at least three looped support struts.

7. The embolic filter of claim 5 further comprising at least three looped support struts.

8. An endoluminal filter assembly comprising
   a filter element;
   a support wire;
   a filter frame comprising at least two "s" shaped support struts attaching the filter element to the support wire via a collar;
   the two "s" shaped supports struts having an elongated configuration and a deployed configuration wherein the two "s" shaped struts each have two opposite bends greater than or equal to 90 degrees wherein the deployed configuration forms an "s" shape with the struts positioned essentially within a plane of an opening of the filter;
   the support struts in the elongated configuration having an essentially linear form.

9. The endoluminal filter assembly of claim 8 wherein the filter frame is slidably attached to the support wire.

10. An embolic filter comprising:
    a filter element;
    a support wire;
    a filter frame comprising at least two "s" shaped support struts attaching the filter element to the support wire via a collar;
    the two "s" shaped struts having two opposite bends greater than or equal to 90 degrees; and
    the two "s" shaped support struts having an elongated configuration wherein the support struts assume a curvilinear configuration and a deployed configuration wherein the deployed configuration forms an "s" shape with the struts positioned essentially within a plane of an opening of the filter.

11. An embolic filter comprising:
    a support wire;
    an embolic filter frame having a longitudinal axis and including multiple support struts affixed to a collar and mounted to the support wire via the collar, the multiple support struts extending radially from the support wire;
    the struts having a constrained delivery state and a non-tensioned deployed state;
    at least one strut having a loop configuration when in the non-tensioned deployed state;
    the at least one strut positioned essentially within a plane of an opening of the filter when in the non-tensioned state;
    the at least one strut having a rotation about the longitudinal axis; and
    a filter element attached to the frame.

* * * * *